US010252266B2

(12) United States Patent
Hung et al.

(10) Patent No.: US 10,252,266 B2
(45) Date of Patent: Apr. 9, 2019

(54) MICROFLUIDIC SIPHONING ARRAY FOR NUCLEIC ACID QUANTIFICATION

(71) Applicant: Combinati Incorporated, Palo Alto, CA (US)

(72) Inventors: Ju-Sung Hung, Palo Alto, CA (US); Andrew Zayac, San Leandro, CA (US); Megan Dueck, Brisbane, CA (US)

(73) Assignee: COMBINATI INCORPORATED, Palo Alto, CA (US)

( * ) Notice: Subject to any disclaimer, the term of this patent is extended or adjusted under 35 U.S.C. 154(b) by 0 days.

(21) Appl. No.: 16/026,827

(22) Filed: Jul. 3, 2018

(65) Prior Publication Data

US 2018/0304254 A1  Oct. 25, 2018

Related U.S. Application Data

(63) Continuation of application No. 15/783,743, filed on Oct. 13, 2017, which is a continuation of application
(Continued)

(51) Int. Cl.
*C12Q 1/68* (2018.01)
*B01L 3/00* (2006.01)
(Continued)

(52) U.S. Cl.
CPC ............. *B01L 3/50273* (2013.01); *B01L 7/52* (2013.01); *C12Q 1/686* (2013.01);
(Continued)

(58) Field of Classification Search
CPC ......... B01L 3/50025; B01L 3/502; B01L 3/50
(Continued)

(56) References Cited

U.S. PATENT DOCUMENTS 5,807,522 A * 9/1998 Brown ....................... B01J 4/02
422/50
6,699,713 B2 3/2004 Benett et al.
(Continued)

FOREIGN PATENT DOCUMENTS

WO WO-2015085181 A1 6/2015
WO WO-2017176699 A1 10/2017
WO WO-2018094091 A1 5/2018

OTHER PUBLICATIONS

Beer et al. On-Chip, Real-Time, Single-Copy Polymerase Chain Reaction in Picoliter Droplets. Anal Chem 79:8471-8475 (2007).
(Continued)

*Primary Examiner* — Christine T Mui
(74) *Attorney, Agent, or Firm* — Wilson Sonsini Goodrich & Rosati

(57) ABSTRACT

In some aspects, the present disclose provides methods for amplifying and quantifying nucleic acids. Methods for amplifying and quantifying nucleic acids comprise isolating a sample comprising nucleic acid molecules into a plurality of microchambers, performing a polymerase chain reaction on the plurality of microchambers, and analyzing the results of the polymerase chain reaction. In some aspects, the present disclosure provides devices consistent with the methods herein.

30 Claims, 10 Drawing Sheets

Specification includes a Sequence Listing.

Related U.S. Application Data

No. PCT/US2017/025873, filed on Apr. 4, 2017, which is a continuation-in-part of application No. 15/363,896, filed on Nov. 29, 2016, now Pat. No. 9,845,499.

(60) Provisional application No. 62/317,993, filed on Apr. 4, 2016.

(51) Int. Cl.
    *C12Q 1/686*     (2018.01)
    *B01L 7/00*     (2006.01)

(52) U.S. Cl.
CPC ............ B01L 2200/0605 (2013.01); B01L 2300/0609 (2013.01); B01L 2300/0851 (2013.01); B01L 2300/0864 (2013.01); B01L 2300/18 (2013.01); B01L 2400/049 (2013.01); B01L 2400/0487 (2013.01)

(58) Field of Classification Search
USPC .............................. 422/500, 509, 82.05, 105
See application file for complete search history.

(56) References Cited

U.S. PATENT DOCUMENTS

| | | | |
|---|---|---|---|
| 7,504,241 B2 | 3/2009 | Atwood et al. | |
| 7,939,312 B2 | 5/2011 | Roberts et al. | |
| 8,871,446 B2 | 10/2014 | Hong et al. | |
| 9,034,635 B2 | 5/2015 | Termaat et al. | |
| 9,213,042 B2* | 12/2015 | Oldham | B01L 3/5027 |
| 9,631,229 B2 | 4/2017 | Stroganov et al. | |
| 9,776,187 B2 | 10/2017 | Atwood et al. | |
| 9,845,499 B2 | 12/2017 | Hung et al. | |
| 2009/0250347 A1* | 10/2009 | Powell | G01N 27/44717 |
| | | | 204/549 |
| 2011/0003699 A1 | 1/2011 | Yoder et al. | |
| 2012/0107818 A1 | 5/2012 | Rothmann et al. | |
| 2014/0291558 A1 | 10/2014 | Laermer et al. | |
| 2014/0323358 A1* | 10/2014 | Oldham | B01L 3/5025 |
| | | | 506/37 |
| 2016/0025761 A1 | 1/2016 | West et al. | |
| 2016/0318023 A1 | 11/2016 | Marble et al. | |

OTHER PUBLICATIONS

Burroughs et al. Chapter 10: Ultra-High-Speed PCR Instrument Development. PCR Technology Current Innovations 3rd Ed. xxpress® (pp. 143-157) (2013).

Espira, Inc. Digital PCR. http://www.espirainc.com/digital-per.html (1 pg.) (Feb. 15, 2017).

Formulatrix. Constellation Digital PCR. http://formulatrix.com/per/index.html (3 pgs.) (Feb. 15, 2017).

JN Medsys, Clarity$^{SM}$ Digital PCR Technology,< http://www.jnmedsys.com/digital-per-description/ (11 pgs.) (Feb. 15, 2017).

Lee et al. Bulk-micromachined submicroliter-volume PCR chip with very rapid thermal response and low power consumption. Lab Chip 4:401-407 (2004).

Men et al. Digital Polymerase Chain Reaction in an Array of Femtoliter Polydimethylsiloxane Microreactors. Anal Chem 84:4262-4266 (2012).

Morrison et al. Nanoliter high through quantitative PCR. Nucleic Acids Res 34(18):e123 (2006).

Ottesen et al. Microfluidic digital PCR enables multigene analysis of individual environmental bacteria. Science 314(5804):1464-1467 (2006).

PCT/US2017/025873 International Search Report and Written Opinion dated Aug. 25, 2017.

PCT/US2017/025873 Invitation to Pay Additional Fees dated Jun. 19, 2017.

PCT/US2017/062078 International Search Report and Written Opinion dated Jan. 30, 2018.

Ramakrishnan et al. Integrated Fluidic Circuits (IFCs) for digital PCR. Methods Mol Biol 949:423-431 (2013).

Saiki et al. Primer-Directed Enzymatic Amplification of DNA with a Thermostable DNA Polymerase. Science 239:487-491 (1988).

Shen et al. Digital PCR on a SlipChip. Lab Chip 10:2666-2672 (2010).

Stilla. Crystal Digital PCR. http://www.stilla.fr/index.html#crystal-digital-per http://www.stilla.fr/index.html (6 pgs.) (Feb. 15, 2017).

Volgelstein et al. Digital PCR. PNAS USA 96:9236-9241 (1999).

Zhang et al. Continuous-Flow PCR Microfluidics for Rapid DNA Amplification Using Thin Film Heater with Low Thermal Mass. Analytical Letters 40(9):1672-1685 (2011).

* cited by examiner

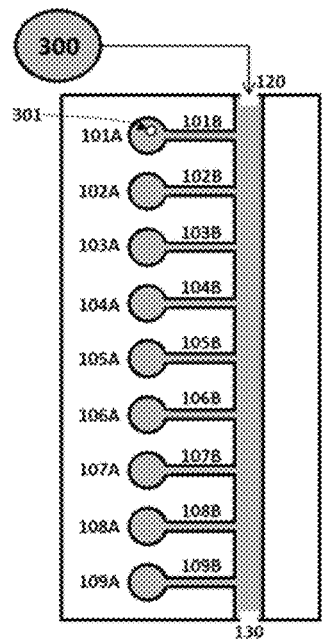
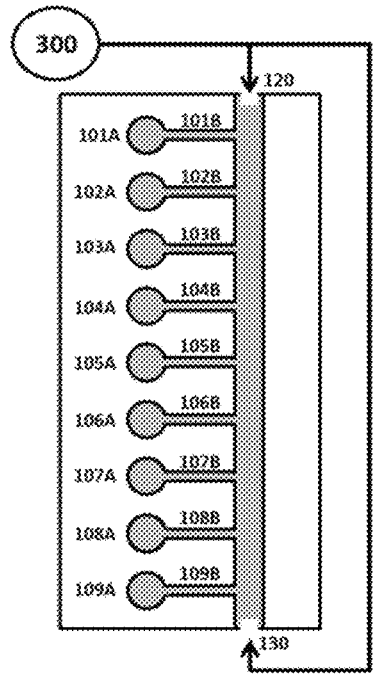
FIG. 3A  FIG. 3B
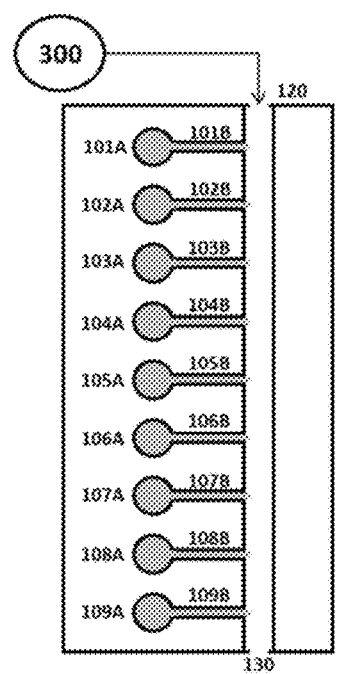
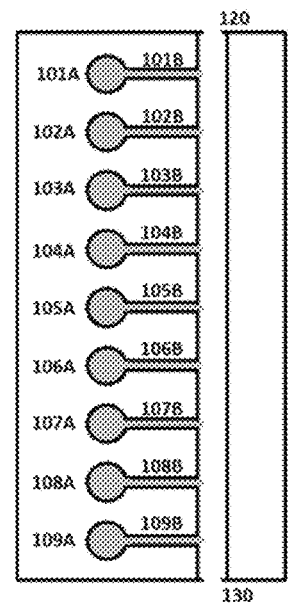
FIG. 3C  FIG. 3D

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcctcaataa agcttgcctt ga                                              22

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggggcgcact gctagaga                                                   18

<210> SEQ ID NO 3
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
ccagagtcac acaacagacg ggcaca                                              26
```

MICROFLUIDIC SIPHONING ARRAY FOR NUCLEIC ACID QUANTIFICATION

CROSS-REFERENCE

This application is a continuation of U.S. patent application Ser. No. 15/783,743, filed Oct. 13, 2017, which is a continuation of PCT Application Serial No. PCT/US2017/025873, filed Apr. 4, 2017, which is a continuation-in-part of U.S. patent application Ser. No. 15/363,896, filed Nov. 29, 2016, which claims priority to U.S. Provisional Patent Application Ser. No. 62/317,993, filed Apr. 4, 2016, each of which is entirely incorporated herein by reference.

GOVERNMENT INTEREST STATEMENT

This invention was made with government support under Small Business Innovation Research grant number 1R43OD023028-01 awarded by the National Institute of Health. The U.S. government has certain rights in the invention.

SEQUENCE LISTING

The instant application contains a Sequence Listing which has been submitted electronically in ASCII format and is hereby incorporated by reference in its entirety. Said ASCII copy, created on Jul. 2, 2018, is named 51674702302SL.txt and is 1,094 bytes in size.

BACKGROUND

Microfluidic devices are devices that contain structures that handle fluids on a small scale. Typically, a microfluidic device operates on a sub-millimeter scale and handles micro-liters, nano-liters, or smaller quantities of fluids. In microfluidic devices, a major fouling mechanism is trapped air, or bubbles, inside the micro-structure. This can be particularly problematic when using a thermoplastic material to create the microfluidic structure, as the gas permeability of thermoplastics is very low.

In order to avoid fouling by trapped air, previous microfluidic structures use either simple straight channel or branched channel designs with thermoplastic materials, or else manufacture the device using high gas permeability materials such as elastomers. However, simple designs limit possible functionality of the microfluidic device, and elastomeric materials are both difficult and expensive to manufacture, particularly at scale.

One application of microfluidic structures is in digital polymerase chain reaction (dPCR). dPCR dilutes a nucleic acid sample down to one or less nucleic acid template in each partition of a microfluidic structure providing an array of many partitions, and performs a PCR reaction across the array. By counting the partitions in which the template was successfully PCR amplified and applying Poisson statistics to the result, the target nucleic acid is quantified. Unlike the popular quantitative real-time PCR (qPCR) where templates are quantified by comparing the rate of PCR amplification of an unknown sample to the rate for a set of known qPCR standards, dPCR has proven to exhibit higher sensitivity, better precision and greater reproducibility.

For genomic researchers and clinicians, dPCR is particularly powerful in rare mutation detection, quantifying copy number variants, and Next Gen Sequencing library quantification. The potential use in clinical settings for liquid biopsy with cell free DNA and viral load quantification further increases the value of dPCR technology. Existing dPCR solutions have used elastomeric valve arrays, silicon through-hole approaches, and microfluidic encapsulation of droplets in oil. Despite the growing number of available dPCR platforms, dPCR has been at a disadvantage when compared to the older qPCR technology which relies on counting the number of PCR amplification cycles. The combination of throughput, ease of use, performance and cost are the major barriers for gaining adoption in the market for dPCR.

SUMMARY

Provided herein are methods and devices that may be useful for amplifying and quantifying nucleic acids. The present disclosure provides methods, systems, and devices that may enable sample preparation, sample amplification, and sample analysis through the use of dPCR. This may enable a nucleic acid to be amplified and quantified at a reduced cost and complexity as compared to other systems and methods.

In an aspect, the present disclosure provides a microfluidic device comprising: at least one microchannel comprising at least one inlet and at least one outlet; a plurality of microchambers and a plurality of siphon apertures, where the plurality of microchambers are in fluid communication with the at least one microchannel by the plurality of siphon apertures; and a thermoplastic thin film disposed adjacent to a surface of the microfluidic device such that the thermoplastic thin film covers the plurality of microchambers, where the thermoplastic thin film is at least partially permeable to a gas under a pressure differential applied across the thermoplastic thin film.

In some embodiments, the at least one microchannel further comprises a plurality of sub-channels in fluid communication with a cross-channel and wherein the plurality of microchambers are in fluid communication with the plurality of sub-channels by the plurality of siphon apertures. In some embodiments, the plurality of sub-channels is substantially parallel to one another such that the plurality of microchambers is in a grid configuration.

In some embodiments, the thermoplastic thin film covers the at least one microchannel and/or the plurality of siphon apertures. In some embodiments, the plurality of siphon apertures has a depth from about 10 micrometers ($\mu$m) to about 20 $\mu$m.

In some embodiments, the plurality of siphon apertures has a depth that is less than about 10 $\mu$m. In some embodiments, the plurality of microchambers has a depth from about 25 $\mu$m to about 75 $\mu$m. In some embodiments, the plurality of microchambers has a depth that is less than about 25 $\mu$m. In some embodiments, the thermoplastic thin film has a thickness from about 50 $\mu$m to about 200 $\mu$m. In some embodiments, plurality of microchambers comprises from about 1,000 to about 20,000 microchambers. In some embodiments, the plurality of microchambers is cylindrical in shape. In some embodiments, the plurality of microchambers is hemispherical in shape.

In some embodiments, the microfluidic device is formed by injection molding. In some embodiments, the thermoplastic thin film is formed by injection molding. In some embodiments, the thermoplastic thin film is applied to the microfluidic device by thermal bonding. In some embodiments, the thermoplastic thin film comprises a cyclo-olefin polymer.

In some embodiments, the pressure differential applied across the thermoplastic thin film is from about 8 pounds per square inch (psi) to about 16 psi. In some embodiments, a pneumatic pump is in fluid communication with the at least one inlet or the at least one outlet. In some embodiments, the microfluidic device does not include valves between the at least one microchannel and the plurality of microchambers.

In an aspect, the present disclosure provides a method for forming a microfluidic device, comprising: injection molding a thermoplastic to generate a microfluidic structure comprising at least one microchannel, a plurality of microchambers, and a plurality of siphon apertures, wherein the plurality of microchambers are in fluid communication with the at least one microchannel by the plurality of siphon apertures; forming at least one inlet and at least one outlet that are in fluid communication with the at least on microchannel; and applying a thermoplastic thin film to cover the plurality of microchambers, where the thermoplastic thin film is at least partially permeable to a gas under a pressure differential applied across the thermoplastic thin film.

In some embodiments, the thermoplastic thin film is formed by injection molding. In some embodiments, the thermoplastic thin film is applied to the microfluidic structure by thermal bonding. In some embodiments, the at least one inlet and at least one outlet are formed by mechanical drilling.

In some embodiments, the at least one microchannel further comprises a plurality of sub-channels in fluid communication with a cross-channel and wherein the plurality of microchambers are in fluid communication with the plurality of sub-channels by the plurality of siphon apertures. In some embodiments, the plurality of sub-channels is substantially parallel to one another such that the plurality of microchambers is in a grid configuration.

In some embodiments, the thermoplastic thin film covers the at least one microchannel and/or the plurality of siphon apertures. In some embodiments, the plurality of siphon apertures has a depth from about 10 µm to about 20 µm. In some embodiments, the plurality of siphon apertures has a depth that is less than about 10 µm. In some embodiments, the plurality of microchambers has a depth from about 25 µm to about 75 µm. In some embodiments, the plurality of microchambers has a depth that is less than about 25 µm. In some embodiments, the thermoplastic thin film has a thickness from about 50 µm to about 200 µm.

In some embodiments, the plurality of microchambers is cylindrical in shape. In some embodiments, the plurality of microchambers is hemispherical in shape.

In some embodiments, the thermoplastic thin film comprises a cyclo-olefin polymer. In some embodiments, the pressure differential applied across the thermoplastic thin film is from about 8 psi to about 16 psi.

In some embodiments, the microfluidic device does not include valves between the at least one microchannel and the plurality of microchambers. In some embodiments, the plurality of microchambers comprises from about 1,000 to about 20,000 microchambers.

In an aspect, the present disclosure provides methods for using a microfluidic device, comprising: (a) providing the microfluidic device comprising at least one microchannel, wherein the at least one microchannel comprises at least one inlet and at least one outlet, and where the microfluidic device further comprises a plurality of microchambers in fluid communication with the at least one microchannel by a plurality of siphon apertures, and a thermoplastic thin film disposed adjacent to a surface of the microfluidic device such that the thermoplastic thin film covers the plurality of microchambers; (b) directing a reagent from the at least one inlet or the at least one outlet to the at least one microchannel under a first pressure differential; (c) directing the reagent into the plurality of microchambers under a second pressure differential between the at least one microchannel and the plurality of microchambers, where upon directing the reagent into the plurality of microchambers, gas within the plurality of microchambers is subjected to flow through the thermoplastic thin film covering the plurality of microchambers; and (d) directing a fluid into the at least one microchannel under a third pressure differential between the at least one inlet and the at least one outlet without introducing the fluid into the plurality of microchambers.

In some embodiments, (a)-(d) are performed using a single integrated machine.

In some embodiments, the thermoplastic thin film covers the at least one microchannel and/or the plurality of siphon apertures.

In some embodiments, the second pressure differential is greater than the first pressure differential. In some embodiments, the third pressure differential is less than the second pressure differential.

In some embodiments, the method further comprises providing a polymerase chain reaction (PCR) reagent comprising nucleic acid molecules to each of the plurality of microchambers. In some embodiments, the method further comprises performing PCR by thermal cycling the plurality of microchambers. In some embodiments, the method further comprises acquiring images of the plurality of microchambers. In some embodiments, the method further comprises counting a number of the plurality of microchambers within which the PCR successfully amplifies the nucleic acid molecules. In some embodiments, the method further comprises applying Poisson statistics to the number of the plurality of microchambers within which the PCR successfully amplifies the PCR reagent to quantify nucleic acids within the PCR reagent.

In some embodiments, the at least one microchannel further comprises a plurality of sub-channels in fluid communication with a cross-channel and wherein the plurality of microchambers are in fluid communication with the plurality of sub-channels by the plurality of siphon apertures. In some embodiments, the plurality of sub-channels is substantially parallel to one another such that the plurality of microchambers is in a grid configuration.

In some embodiments, the third pressure differential is from about 1 psi to about 4 psi. In some embodiments, the second pressure differential is from about 8 psi to about 16 psi. In some embodiments, the thermoplastic thin film comprises a cyclo-olefin polymer.

In some embodiments, the plurality of microchambers comprises from about 1,000 to about 20,000 microchambers. In some embodiments, the plurality of microchambers is cylindrical in shape. In some embodiments, the plurality of microchambers is hemispherical in shape. In some embodiments, the microfluidic device does not include valves between the at least one microchannel and the plurality of microchambers.

In some embodiments, the plurality of siphon apertures has a depth from about 10 µm to about 20 µm. In some embodiments, the plurality of siphon apertures has a depth that is less than about 10 µm. In some embodiments, the plurality of microchambers has a depth from about 25 µm to about 75 µm. In some embodiments, the plurality of microchambers has a depth that is less than about 25 µm. In some embodiments, the thermoplastic thin film has a thickness from about 50 µm to about 200 µm.

In some embodiments, the fluid is air, nitrogen, carbon dioxide, a noble gas, or any combination thereof.

In an aspect, the present disclosure provides a system for using a microfluidic device, comprising: a transfer stage configured to hold at least one microfluidic device comprising (i) at least one microchannel, where the at least one microchannel comprises at least one inlet and at least one outlet, (ii) a plurality of microchambers in fluid communication with the at least one microchannel by a plurality of siphon apertures, and (ii) a thermoplastic thin film covering the plurality of microchambers; a pneumatic module in fluid communication with the at least one microfluidic device, where the pneumatic module is configured to load a reagent into the microfluidic device for partitioning into the plurality of microchambers; a thermal module in thermal communication with the plurality of microchambers, where the thermal module is configured to control a temperature of and thermal cycle the plurality of microchambers; an optical module configured to image the plurality of microchambers of the microfluidic device; and one or more computer processors coupled to the transfer stage, the pneumatic module, the thermal module, and the optical module, where the one or more computer processors are individually or collectively programmed to (i) direct the pneumatic module to load the reagent into the microfluidic device for partitioning into the plurality of microchambers, (ii) direct the thermal module to thermal cycle the plurality of microchambers, and (iii) direct the optical module to image the plurality of microchambers.

In some embodiments, the at least one microfluidic device does not include valves between the at least one microchannel and the plurality of microchambers. In some embodiments, the thermoplastic thin film covers the at least one microchannel and/or the plurality of siphon apertures.

In some embodiments, the pneumatic module is further configured to apply a first pressure differential to load the reagent into the at least one microchannel. In some embodiments, the pneumatic module is further configured to apply a second pressure differential between the at least one microchannel and the plurality of microchambers to partition the reagent into the plurality of microchambers. In some embodiments, the pneumatic module is further configured to apply a third pressure differential between the at least one inlet and the at least one outlet to subject a fluid to flow into the at least one microchannel. In some embodiments, the second pressure differential is from about 8 psi to about 16 psi. In some embodiments, the third pressure differential is from about 1 psi to about 4 psi.

In some embodiments, the optical module is configured to image at least two different wavelength ranges. In some embodiments, a first of the at least two different wavelength ranges is used to verify the reagent partitioning. In some embodiments, a second of the at least two different wavelength ranges is used to detect a reaction within the plurality of microchambers.

In an aspect, the present disclosure provides a method for using a microfluidic device, comprising: providing the microfluidic device comprising a microchannel, where the microchannel comprises at least one inlet and at least one outlet, and where the microfluidic device further comprises a plurality of microchambers connected to the microchannel by a plurality of siphon apertures, and a thermoplastic thin film disposed adjacent to the microfluidic device such that the thermoplastic thin film caps the microchannel, the plurality of microchambers, and the plurality of siphon apertures; filling the plurality of microchambers of the microfluidic device with a reagent by applying the reagent at a first pressure to the at least one inlet; applying a high pressure gas at a second pressure (e.g., 8 psi to 16 psi) at the at least on inlet or at the at least one outlet to force gas within the plurality of microchambers, the plurality of siphon apertures, and the microchannel, where the second pressure is greater than the first pressure; and applying a low pressure gas (e.g., pressure less than the high pressure gas) at a third pressure (e.g., from 1 psi to 4 psi) at the at least one inlet to introduce the low pressure gas into the microchannel without introducing the low pressure gas into the plurality of microchambers, where the third pressure is less than the second pressure.

In some embodiments, method is performed using a single integrated machine. In some embodiments, the method further comprises proving a PCR reagent comprising nucleic acid molecules to each of the plurality of microchambers. In some embodiments, the method further comprises performing PCR by thermal cycling the plurality of microchambers. In some embodiments, the method further comprises acquiring images of the plurality of microchambers. In some embodiments, the method further comprises counting a number of the plurality of microchambers within which the PCR successfully amplifies the nucleic acid molecules. In some embodiments, the method further comprises applying Poisson statistic to the number of the plurality of microchambers within which the PCR successfully amplifies the PCR reagent to quantify nucleic acids within the PCR reagent.

In some embodiments, the microchannel comprises a plurality of sub-channels connected via a cross-channel and wherein the plurality of microchambers is connected to the plurality of sub-channels. In some embodiments, the plurality of sub-channels is substantially parallel to one another such that the plurality of microchambers is in a grid configuration.

In some embodiments, the third pressure is between about 1 psi and 4 psi. In some embodiments, the second pressure is between about 8 psi and 16 psi. In some embodiments, the high pressure gas comprises air, nitrogen, carbon dioxide, a noble gas, or any combination thereof. In some embodiments, the thermoplastic thin film comprises a cyclo-olefin polymer. In some embodiments, a pneumatic pump is in fluid communication with the at least one inlet or the at least one outlet.

In some embodiments, the plurality of microchambers comprises between 1,000 and 20,000 microchambers. In some embodiments, the plurality of microchambers is cylindrical in shape. In some embodiments, the microfluidic device is formed by injection molding.

In some embodiments, the thermoplastic thin film is formed by injection molding.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1A shows the structure from an overhead view, while FIG. 1B illustrates a cross-section of the structure;

FIG. 2A shows an embodiment in which parallel sub-channels and one or more cross-channels are used to form a grid of microchambers; FIG. 2B shows an embodiment in which a single microchannel in a serpentine pattern forms a hexagonal grid of microchambers;

FIGS. 3A-3D show methods for use of an example microfluidic device; FIG. 3A shows a step of applying reagent at low pressure; FIG. 3B shows a step of applying a pressure differential across the microfluidic device to force partitioning and outgassing; FIG. 3C shows a step of applying fluid at low pressure to clear the microchannel; FIG. 3D shows the state of the system after the completion of the method;

FIG. 8A shows a microfluidic device formed by micromolding a thermoplastic; FIG. 8B show fluorescent images of the sample partitioning process;

FIG. 10A shows zero copies per partition (NTC) after amplification; FIG. 10B shows nucleic acid amplification of partitions containing approximately one copy per partition; FIG. 10C shows a plot of NTC fluorescence intensity of both fluorescent colors; and FIG. 10D shows a plot of fluorescence intensity of both fluorescent colors of the amplified sample.

DETAILED DESCRIPTION

Figure 1A:
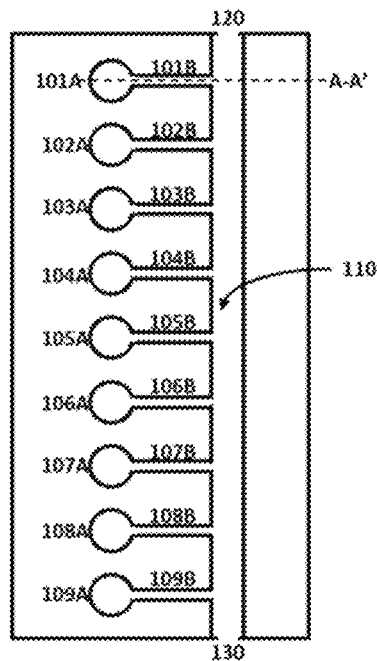
FIGS. 1A and 1B illustrate an example of a microfluidic structure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the terms "amplification" and "amplify" are used interchangeably and generally refer to generating one or more copies or "amplified product" of a nucleic acid. Such amplification may be using polymerase chain reaction (PCR) or isothermal amplification, for example.

As used herein, the term "nucleic acid" generally refers to a polymeric form of nucleotides of any length (e.g., at least 2, 3, 4, 5, 6, 7, 8, 9, 10, 100, 500, or 1000 nucleotides), either deoxyribonucleotides or ribonucleotides, or analogs thereof. A nucleic acid may include one or more subunits selected from adenosine (A), cytosine (C), guanine (G), thymine (TO, and uracil (U), or variants thereof. A nucleotide can include A, C, G, T, or U, or variants thereof. A nucleotide can include any subunit that can be incorporated into a growing nucleic acid strand. Such subunit can be A, C, G, T, or U, or any other subunit that is specific to one of more complementary A, C, G, T, or U, or complementary to a purine (i.e., A or G, or variant thereof) or pyrimidine (i.e., C, T, or U, or variant thereof). In some examples, a nucleic acid may be single-stranded or double stranded, in some cases, a nucleic acid molecule is circular. Non-limiting examples of nucleic acids include DNA and RNA. Nucleic acids can include coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs.

As used herein, the terms "polymerase chain reaction reagent" or "PCR reagent" are used interchangeably and generally refer to a composition comprising reagents necessary to complete a nucleic acid amplification reaction (e.g., DNA amplification), with non-limiting examples of such reagents including primer sets or priming sites (e.g., nick) having specificity for a target nucleic acid, polymerases, suitable buffers, co-factors (e.g., divalent and monovalent cations), dNTPs, and other enzymes. A PCR reagent may also include probes, indicators, and molecules that comprise probes and indicators.

As used herein, the term "probe" generally refers to a molecule that comprises a detectable moiety, the presence or absence of which may be used to detect the presence or absence of an amplified product. Non-limiting examples of detectable moieties may include radiolabels, stable isotope labels, fluorescent labels, chemiluminescent labels, enzymatic labels, colorimetric labels, or any combination thereof.

As used herein, the term "extension" generally refers to incorporation of nucleotides into a nucleic acid in a template directed fashion. Extension may occur via the aid of an enzyme. For example, extension may occur via the aid of a polymerase. Conditions at which extension may occur include an "extension temperature" that generally refers to a temperature at which extension is achieved and an "extension duration" that generally refers to an amount of time allotted for extension to occur.

As used herein, the term "indicator molecule" generally refers to a molecule that comprises a detectable moiety, the presence or absence of which may be used to indicate sample partitioning. Non-limiting examples of detectable moieties may include radiolabels, stable isotope labels, fluorescent labels, chemiluminescent labels, enzymatic labels, colorimetric labels, or any combination thereof.

The term "sample," as used herein, generally refers to any sample containing or suspected of containing a nucleic acid molecule. For example, a sample can be a biological sample containing one or more nucleic acid molecules. The biological sample can be obtained (e.g., extracted or isolated) from or include blood (e.g., whole blood), plasma, serum, urine, saliva, mucosal excretions, sputum, stool and tears. The biological sample can be a fluid or tissue sample (e.g., skin sample). In some examples, the sample is obtained from a cell-free bodily fluid, such as whole blood. In such instance, the sample can include cell-free DNA and/or cell-free RNA. In some examples, the sample can include circulating tumor cells. In some examples, the sample is an environmental sample (e.g., soil, waste, ambient air and etc.), industrial sample (e.g., samples from any industrial processes), and food samples (e.g., dairy products, vegetable products, and meat products).

As used herein, the term "fluid" generally refers to a liquid or a gas. A fluid cannot maintain a defined shape and will flow during an observable time frame to fill the container into which it is put. Thus, the fluid may have any suitable viscosity that permits flow. If two or more fluids are present, each fluid may be independently selected among essentially any fluids (liquids, gases, and the like) by those of ordinary skill in the art.

As used herein, the term "partition" generally refers to a division into or distribution into portions or shares. For example, a partitioned sample is a sample that is isolated from other samples. Examples of structures that enable sample partitioning include wells and microchambers.

As used herein, the term "microfluidic" generally refers to a chip, area, device, article, or system including at least one microchannel, a plurality of siphon apertures, and an array of microchambers. The microchannel may have a cross-sectional dimension less than or equal to about 10 millimeters (mm), less than or equal to about 5 mm, less than or equal to about 4 mm, less than or equal to about 3 mm, less than or equal to about 2 mm, less than or equal to about 1.5 mm, less than or equal to about 1 mm, less than or equal to about 750 micrometers (μm), less than or equal to about 500 μm, less than or equal to about 250 μm, less than or equal to about 100 μm, or less.

As used herein, the term "depth" generally refers to the distance measured from the bottom of the microchannel, siphon aperture, or microchamber to the thin film that caps the microchannel, plurality of siphon apertures, and array of microchambers.

As used herein, the terms "cross-section" or "cross-sectional" may be used interchangeably and generally refer to a dimension or area of a microchannel or siphon aperture that is substantially perpendicularly to the long dimension of the feature.

The present disclosure describes a microfluidic device formed out of a thermoplastic and incorporating a thin film to allow for pressurized outgassing while serving as a gas barrier when pressure is released. The use of thermoplastic to form the microfluidic structure may allow for the use of an inexpensive and highly scalable injection molding process, while the thin film may provide the ability to outgas via pressurization, avoiding the fouling problems that may be present some microfluidic structures that do not incorporate such thin films.

One use for this structure is a microfluidic design incorporating an array of dead-ended microchambers connected by microchannels, formed out of thermoplastics. This design can be used in a dPCR application to partition reagents into the array of microchambers and thereby used to quantify nucleic acids in dPCR.

Microfluidic Device for Analyzing Nucleic Acid Samples

In an aspect, the present disclosure provides a microfluidic device for analyzing nucleic acid samples. The device may comprise a microchannel connected to an inlet and an outlet. The microfluidic device may also include a plurality of microchambers and a plurality of siphon apertures. The plurality of microchambers may be connected to the microchannel by the plurality of siphon apertures. The microfluidic device may include a thermoplastic thin film which caps and seals (e.g., hermetically seals) the microchannel, microchambers, and siphon apertures. The thermoplastic thin film may be at least partially gas permeable when a pressure differential is applied across the thermoplastic thin film.

Figure 1B:
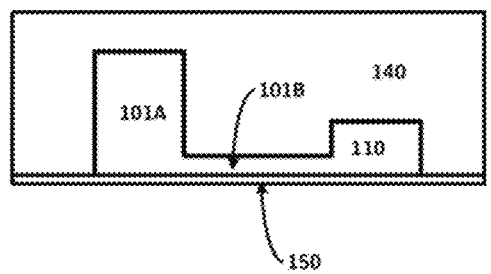

FIGS. 1A and 1B show examples of a microfluidic structure according to certain embodiments of the present disclosure. FIG. 1A shows an example microfluidic device from a top view. The microfluidic device comprises a microchannel 110, with an inlet 120, and an outlet 130. The microchannel is connected to a plurality of siphon apertures 101B-109B. The plurality of siphon apertures connects the microchannel to a plurality of microchambers 101A-109A. FIG. 1B shows a cross-sectional view of a single microchamber along the dashed line marked A-A'. The single microchamber 101A is connected to the microchannel 110 by a siphon aperture 101B. The microfluidic device body 140 may be formed from a rigid plastic material. The microstructures of the microfluidic device may be capped and sealed by a thin film 150. The thin film may be gas impermeable when a small pressure differential is applied across the film and gas permeable when a large pressure differential is applied across the film. This may allow for outgassing through the thin film when a pressure is applied to the interior structure of the microfluidic device. In an alternative embodiment, outgassing may occur when a vacuum is applied external to the microfluidic device.

The gas permeability of the thin film may be induced by elevated pressures. In some embodiments the pressure induced gas permeable thin film may cover the array of microchambers and the microchannel and siphon apertures may be covered by a non-gas permeable film. In some embodiments, the pressure induced gas permeable thin film may cover the array of microchambers and the siphon apertures and the microchannel may be covered by a non-gas permeable film. Alternatively, the pressure induced gas permeable thin film may cover the array of microchambers, the siphon apertures, and the microchannel. In some embodiments, the thickness of the thin film may be less than or equal to about 500 micrometers (μm), less than or equal to about 250 μm, less than or equal to about 200 μm, less than or equal to about 150 μm, less than or equal to about 100 μm, less than or equal to about 75 μm, less than or equal to about 50 μm, less than or equal to about 25 μm, or less. In some embodiments, the thickness of the thin film may be from about 0.1 μm to about 200 μm or about 0.5 μm to about 150 μm. In some examples, the thickness of the thin film may be from about 50 μm to about 200 μm. In some examples, the thickness of the thin film may be from about 100 μm to about 200 μm. In some examples, the thickness of the thin film is about 100 μm to about 150 μm. In an example, the thin film is approximately 100 μm in thickness. The thickness of the film may be selected by manufacturability of the thin film, the air permeability of the thin film, the volume of each partition to be out-gassed, the available pressure, and/or the desired time to complete the siphoning process.

In some embodiments, the microfluidic device may comprise a single array of microchambers. In some embodiments, the microfluidic device may comprise multiple arrays of microchambers, each array of microchambers isolated from the others. The arrays of microchambers may be arranged in a row, in a grid configuration, in an alternating pattern, or in any other configuration. In some embodiments, the microfluidic device may have at least about 1, at least about 2, at least about 3, at least about 4, at least about 5, at least about 10, at least about 15, at least about 20, at least about 30, at least about 40, at least about 50, or more arrays of microchambers. In some embodiments, the arrays of microchambers are identical. In some embodiments, the microfluidic device may comprise multiple arrays of microchambers that are not identical. The arrays of microchambers may all have the same external dimension (i.e., the length and width of the array of microchambers that encompasses all features of the array of microchambers) or the arrays of microchambers may have different external dimensions.

In some embodiments, an array of microchambers may have a width of at most about 100 mm, about 75 mm, about 50 mm, about 40 mm, about 30 mm, about 20 mm, about 10 mm, about 8 mm, about 6 mm, about 4 mm, about 2 mm, about 1 mm, or less. The array of microchambers may have a length of at most about 50 mm, about 40 mm, about 30 mm, about 20 mm, about 10 mm, about 8 mm, about 6 mm, about 4 mm, about 2 mm, 1 mm, or less. The width may be from about 1 mm to 100 mm, or 10 mm to 50 mm. The length may be from about 1 mm to 50 mm, or 5 mm to 20 mm.

In some examples, the array of microchambers may have a width of about 100 mm and a length of about 40 mm. In some examples, the array of microchambers may have a width of about 80 mm and a length of about 30 mm. In some examples, the array of microchambers may have a width of about 60 mm and a length of about 25 mm. In some examples, the array of microchambers may have a width of about 40 mm and a length of about 15 mm. In some examples, the array of microchambers may have a width of about 30 mm and a length of about 10 mm. In some examples, the array of microchambers may have a width of about 20 mm and a length of about 8 mm. In some examples, the array of microchambers may have a width of about 10 mm and a length of about 4 mm. The external dimension may be determined by the total number of microchambers desired, the dimension of each microchamber, and the minimum distance between each microchamber for manufacturability.

In some embodiments, the microchannel is substantially parallel to the long dimension of the microfluidic device. In some embodiments, the microchannel may be substantially perpendicular to the long dimension of the microfluidic device. In some embodiments, the microchannel may be neither substantially parallel nor substantially perpendicular to the long dimension of the microfluidic device. The angle between the microchannel and the long dimension of the microfluidic device may be at least about 5°, at least about 10°, at least about 15°, at least about 20°, at least about 30°, at least about 40°, at least about 50°, at least about 60°, at least about 70°, at least about 90°, at least about 100°, at least about 110°, at least about 120°, at least about 130°, at least about 140°, at least about 150°, at least about 160°, or at least about 170°. In some embodiments, the microchannel may be a single long channel. In some embodiments, the microchannel may have bends, curves, or angles. The microchannel may have a long dimension that is less than or equal to 100 mm, less than or equal to about 75 mm, less than or equal to about 50 mm, less than or equal to about 40 mm, less than or equal to about 30 mm, less than or equal to about 20 mm, less than or equal to about 10 mm, less than or equal to about 8 mm, less than or equal to about 6 mm, less than or equal to about 4 mm, less than or equal to about 2 mm, or less. The length of the microchannel may be bounded by the external length or width of the microfluidic device. The microchannel may have a depth of less than or equal to about 500 µm, less than or equal to about 250 µm, less than or equal to about 100 µm, less than or equal to about 80 µm, less than or equal to about 60 µm, less than or equal to about 30 µm, less than or equal to about 20 µm, less than or equal to about 10 µm, or less. The microchannel may have a cross-sectional dimension (e.g., width) of less than or equal to about 500 µm, less than or equal to about 250 µm, less than or equal to about 100 µm, less than or equal to about 75 µm, less than or equal to about 50 µm, less than or equal to about 40 µm, less than or equal to about 30 µm, less than or equal to about 20 µm, less than or equal to about 10 µm, or less.

In some examples, the cross-sectional dimensions of the microchannel may be about 100 µm wide by about 100 µm deep. In some examples, the cross-sectional dimensions of the microchannel may be about 100 µm wide by about 80 µm deep. In some examples, the cross-sectional dimensions of the microchannel may be about 100 µm wide by about 60 µm deep. In some examples, the cross-sectional dimensions of the microchannel may be about 100 µm wide by about 40 µm deep. In some examples, the cross-sectional dimensions of the microchannel may be about 100 µm wide by about 20 µm deep. In some examples, the cross-sectional dimensions of the microchannel may be about 100 µm wide by about 10 µm deep. In some examples, the cross-sectional dimensions of the microchannel may be about 80 µm wide by about 100 µm deep. In some examples, the cross-sectional dimensions of the microchannel may be about 60 µm wide by about 100 µm deep. In some examples, the cross-sectional dimensions of the microchannel may be about 40 µm wide by about 100 µm deep. In some examples, the cross-sectional dimensions of the microchannel may be about 20 µm wide by about 100 µm deep. In some examples, the cross-sectional dimensions of the microchannel may be about 10 µm wide by about 100 µm deep. In some examples, the cross-sectional dimensions of the microchannel may be about 80 µm wide by about 80 µm deep. In some examples, the cross-sectional dimensions of the microchannel may be about 60 µm wide by about 60 µm deep. In some examples, the cross-sectional dimensions of the microchannel may be about 40 µm wide by about 40 µm deep. In some examples, the cross-sectional dimensions of the microchannel may be about 20 µm wide by about 20 µm deep. In some examples, the cross-sectional dimensions of the microchannel may be about 10 µm wide by about 10 µm deep. The cross-sectional shape of the microchannel may be any suitable cross-sectional shape including, but not limited to, circular, oval, triangular, square, or rectangular. The cross-sectional area of the microchannel may be constant along the length of the microchannel. Alternatively, or in addition to, the cross-sectional area of the microchannel may vary along the length of the microchannel. The cross-sectional area of the microchannel may vary between about 50% and 150%, between about 60% and 125%, between about 70% and 120%, between about 80% and 115%, between about 90% and 110%, between about 95% and 100%, or between about 98% and 102%. The cross-sectional area of the microchannel may be less than or equal to about 10,000 micrometers squared ($\mu m^2$), less than or equal to about 7,500 $\mu m^2$, less than or equal to about 5,000 $\mu m^2$, less than or equal to about 2,500 $\mu m^2$, less than or equal to about 1,000 $\mu m^2$, less than or equal to about 750 $\mu m^2$, less than or equal to about 500 $\mu m^2$, less than or equal to about 400 $\mu m^2$, less than or equal to about 300 $\mu m^2$, less than or equal to about 200 $\mu m^2$, less than or equal to about 100 $\mu m^2$, or less.

In some embodiments, the microchannel may have a single inlet and a single outlet. Alternatively, the microchannel may have multiple inlets, multiple outlets, or multiple inlets and multiple outlets. The inlets and outlets may have the same diameter or they may have different diameters. The inlets and outlets may have diameters less than or equal to about 2.5 millimeters (mm), less than or equal to about 2 mm, less than or equal to about 1.5 mm, less than or equal to about 1 mm, less than about 0.5 mm, or less.

In some embodiments, the array of microchambers may have at least about 1,000 microchambers, at least about 5,000 microchambers, at least about 10,000 microchambers, at least about 20,000 microchambers, at least about 30,000 microchambers, at least about 40,000 microchambers, at least about 50,000 microchambers, at least about 100,000 microchambers, or more. In some examples, the microfluidic device may have from about 10,000 to about 30,000 microchambers. In some examples, the microfluidic device may have from about 15,000 to about 25,000 microchambers. The microchambers may be cylindrical in shape, hemispherical in shape, or a combination of cylindrical and hemispherical in shape. The microchambers may have diameters of less than or equal to about 500 $\mu m$, less than or equal to about 250 $\mu m$, less than or equal to about 100 $\mu m$, less than or equal to about 80 $\mu m$, less than or equal to about 60 $\mu m$, less than or equal to about 30 $\mu m$, less than or equal to about 15 $\mu m$, or less. The depth of the microchambers may be less than or equal to about 500 $\mu m$, less than or equal to about 250 $\mu m$, less than or equal to about 100 $\mu m$, less than or equal to about 80 $\mu m$, less than or equal to about 60 $\mu m$, less than or equal to about 30 $\mu m$, less than or equal to about 15 $\mu m$, or less. In some examples, the microchambers may have a diameter of about 30 $\mu m$ and a depth of about 100 $\mu m$. In some examples, the microchambers may have a diameter of about 35 $\mu m$ and a depth of about 80 $\mu m$. In some examples, the microchambers may have a diameter of about 40 $\mu m$ and a depth of about 70 $\mu m$. In some examples, the microchambers may have a diameter of about 50 $\mu m$ and a depth of about 60 $\mu m$. In some examples, the microchambers may have a diameter of about 60 $\mu m$ and a depth of about 40 $\mu m$. In some examples, the microchambers may have a diameter of about 80 $\mu m$ and a depth of about 35 $\mu m$. In some examples, the microchambers may have a diameter of about 100 $\mu m$ and a depth of about 30 $\mu m$. In some embodiments, the microchambers and the microchannel have the same depth. In an alternative embodiment, the microchambers and the microchannel have different depths.

In some embodiments, the lengths of the siphon apertures are constant. In some embodiments, the lengths of the siphon apertures vary. The siphon apertures may have a long dimension that is less than or equal to about 150 $\mu m$, less than or equal to about 100 $\mu m$, less than or equal to about 50 $\mu m$, less than or equal to about 25 $\mu m$, less than or equal to about 10 $\mu m$, less than or equal to about 5 $\mu m$, or less. In some embodiments, the depth of the siphon aperture may be less than or equal to about 50 $\mu m$, less than or equal to about 25 $\mu m$, less than or equal to about 10 $\mu m$, less than or equal to about 5 $\mu m$ or less. The siphon apertures may have a cross-sectional width less than or equal to about 50 $\mu m$, less than or equal to about 40 $\mu m$, less than or equal to about 30 $\mu m$, less than or equal to about 20 $\mu m$, less than or equal to about 10 $\mu m$, less than or equal to about 5 $\mu m$, or less.

In some examples, the cross-sectional dimensions of the siphon aperture may be about 50 $\mu m$ wide by about 50 $\mu m$ deep. In some examples, the cross-sectional dimensions of the siphon aperture may be about 50 $\mu m$ wide by about 40 $\mu m$ deep. In some examples, the cross-sectional dimensions of the siphon aperture may be about 50 $\mu m$ wide by about 30 $\mu m$ deep. In some examples, the cross-sectional dimensions of the siphon aperture may be about 50 $\mu m$ wide by about 20 $\mu m$ deep. In some examples, the cross-sectional dimensions of the siphon aperture may be about 50 $\mu m$ wide by about 10 $\mu m$ deep. In some examples, the cross-sectional dimensions of the siphon aperture may be about 50 $\mu m$ wide by about 5 $\mu m$ deep. In some examples, the cross-sectional dimensions of the siphon aperture may be about 40 $\mu m$ wide by about 50 $\mu m$ deep. In some examples, the cross-sectional dimensions of the siphon aperture may be about 30 $\mu m$ wide by about 50 $\mu m$ deep. In some examples, the cross-sectional dimensions of the siphon aperture may be about 20 $\mu m$ wide by about 50 $\mu m$ deep. In some examples, the cross-sectional dimensions of the siphon aperture may be about 10 $\mu m$ wide by about 50 $\mu m$ deep. In some examples, the cross-sectional dimensions of the siphon aperture may be about 5 $\mu m$ wide by about 50 $\mu m$ deep. In some examples, the cross-sectional dimensions of the siphon aperture may be about 40 $\mu m$ wide by about 40 $\mu m$ deep. In some examples, the cross-sectional dimensions of the siphon aperture may be about 30 $\mu m$ wide by about 30 $\mu m$ deep. In some examples, the cross-sectional dimensions of the siphon aperture may be about 20 $\mu m$ wide by about 20 $\mu m$ deep. In some examples, the cross-sectional dimensions of the siphon aperture may be about 10 $\mu m$ wide by about 10 $\mu m$ deep. In some examples, the cross-sectional dimensions of the siphon aperture may be about 5 $\mu m$ wide by about 5 $\mu m$ deep. The cross-sectional shape of the siphon aperture may be any suitable cross-sectional shape including, but not limited to, circular, oval, triangular, square, or rectangular. In some embodiments, the cross-sectional area of the siphon aperture may be constant along the length of the siphon aperture. Alternatively, or in addition to, the cross-sectional area of the siphon aperture may vary along the length of the siphon aperture. The cross-sectional area of the siphon aperture may be greater at the connection to the microchannel than the cross-sectional area of the siphon aperture at the connection to the microchamber. Alternatively, the cross-sectional area of the siphon aperture at the connection to the microchamber may be greater than the cross-sectional area of the siphon aperture at the connection to the microchannel. The cross-sectional area of the siphon aperture may vary between about 50% and 150%, between about 60% and 125%, between about 70% and 120%, between about 80% and 115%, between about 90% and 110%, between about 95% and 100%, or between about 98% and 102%. The cross-sectional area of the siphon aperture may be less than or equal to about 2,500 $\mu m^2$, less than or equal to about 1,000 $\mu m^2$, less than or equal to about 750 $\mu m^2$, less than or equal to about 500 $\mu m^2$, less than or equal to about 250 $\mu m^2$, less than or equal to about 100 $\mu m^2$, less than or equal to about 75 $\mu m^2$, less than or equal to about 50 $\mu m^2$, less than or equal to about 25 $\mu m^2$, or less. The cross-sectional area of the siphon aperture at the connection to the microchannel may be less than or equal to the cross-sectional area of the microchannel. The cross-sectional area of the siphon aperture at the connection to the microchannel may be less than or equal to about 98%, less than or equal to about 95%, less than or equal to about 90%, less than or equal to about 85%, less than or equal to about 80%, less than or equal to about 75%, less than or equal to about 70%, less than or equal to about 60%, less than or equal to about 50%, less than or equal to about 40%, less than or equal to about 30%, less than or equal to about 20%, less than or equal to about 10%, less than or equal to about 5%, less than or equal to about 1%, or less than or equal to about 0.5% of the cross-sectional area of the microchannel.

In some embodiments, the siphon apertures are substantially perpendicular to the microchannel. In some embodiments, the siphon apertures are not substantially perpendicular to the microchannel. In some embodiments, an angle between the siphon apertures and the microchannel may be at least about 5°, at least about 10°, at least about 15°, at least about 20°, at least about 30°, at least about 40°, at least about 50°, at least about 60°, at least about 70°, at least about 90°, at least about 100°, at least about 110°, at least about 120°, at least about 130°, at least about 140°, at least about 150°, at least about 160°, or at least about 170°.

Figure 2A:
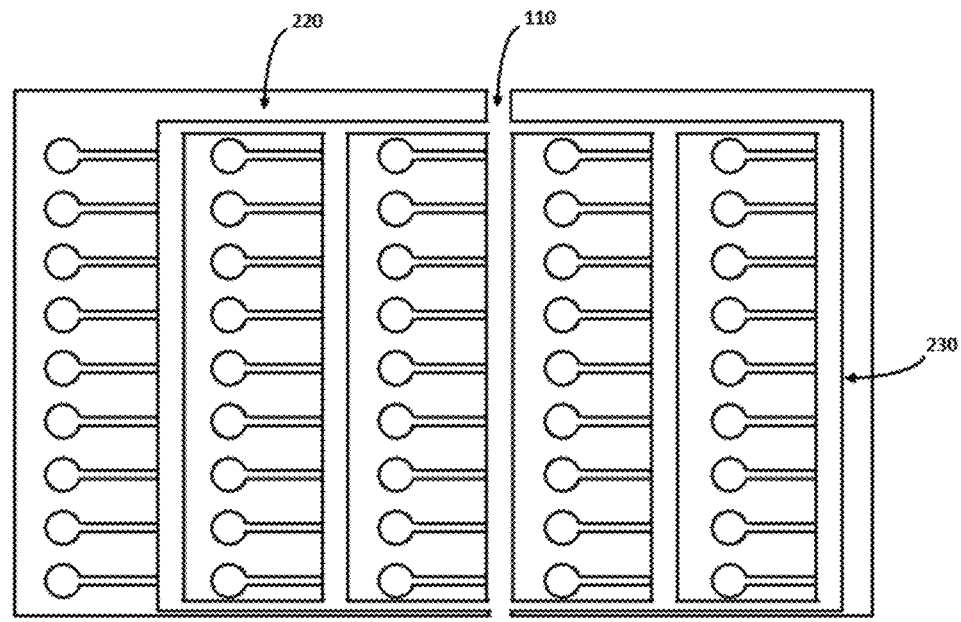
FIGS. 2A and 2B schematically illustrates example arrangements of microchambers, siphon apertures, and microchannels within a microfluidic device.
Figure 2B:
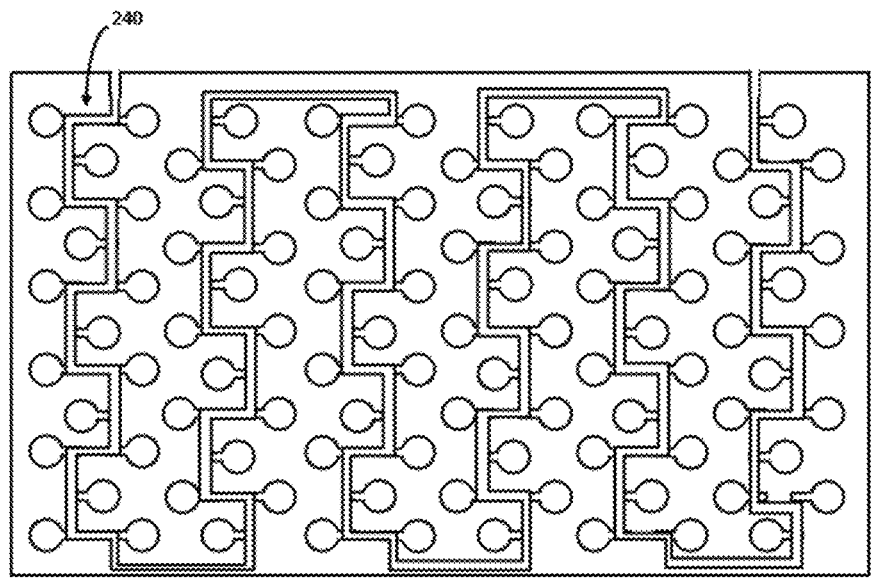

The microchambers may be arranged in a variety of patterns. FIGS. 2A and 2B illustrate exemplary patterns of microchamber, siphon aperture, and microchannel arrangements. In some embodiments, multiple microchannels are employed, while in some embodiments, a single microchannel may be used. In some embodiments, a microchannel may comprise a group of sub-channels. The group of sub-channels may be connected by one or more cross-channels. In some of these embodiments, the sub-channels are substantially parallel to one another so that the array of microchambers forms a grid of microchambers. FIG. 2A illustrates an embodiment in which parallel sub-channels 230 and one or more cross-channels 220 are used to form a grid of microchambers.

In some embodiments, microchambers are constructed so as to form a hexagonal grid of microchambers, with curved or angled sub-channels connecting the microchambers. A hexagonal grid of microchambers may also be formed and connected by a single microchannel, such as by a microchannel that forms a serpentine pattern 240 across the microfluidic device. FIG. 2B illustrates an embodiment in which a single microchannel in a serpentine pattern forms a hexagonal grid of microchambers.

In some embodiments, the lengths of the sub-channels are constant. In some embodiments, the lengths of the sub-channel may vary. The sub-channel may have a long dimension that is less than or equal to 100 mm, less than or equal to about 75 mm, less than or equal to about 50 mm, less than or equal to about 40 mm, less than or equal to about 30 mm, less than or equal to about 20 mm, less than or equal to about 10 mm, less than or equal to about 8 mm, less than or equal to about 6 mm, less than or equal to about 4 mm, less than or equal to about 2 mm, or less. The length of the sub-channel may be bounded by the external length or width of the microfluidic device. In some embodiments, the sub-channel may have the same cross-sectional dimension as the microchannel. In some embodiments, the sub-channel may have different cross-sectional dimension than the microchannel. In some embodiments, the sub-channel may have the same depth as the microchannel and a different cross-sectional dimension. In some embodiments, the sub-channel may have the same cross-sectional dimension as the microchannel and a different depth. For example, the sub-channel may have a depth of less than or equal to about 500 µm, less than or equal to about 250 µm, less than or equal to about 100 µm, less than or equal to about 80 µm, less than or equal to about 60 µm, less than or equal to about 30 µm, less than or equal to about 15 µm, or less. The sub-channel may have a cross-section width of less than or equal to about 500 µm, less than or equal to about 250 µm, less than or equal to about 100 µm, less than or equal to about 75 µm, less than or equal to about 50 µm, less than or equal to about 40 µm, less than or equal to about 30 µm, less than or equal to about 20 µm, less than or equal to about 10 µm, or less.

In some examples, the cross-sectional dimensions of the sub-channel may be about 100 µm wide by about 100 µm deep. In some examples, the cross-sectional dimensions of the sub-channel may be about 100 µm wide by about 80 µm deep. In some examples, the cross-sectional dimensions of the sub-channel may be about 100 µm wide by about 60 µm deep. In some examples, the cross-sectional dimensions of the sub-channel may be about 100 µm wide by about 40 µm deep. In some examples, the cross-sectional dimensions of the sub-channel may be about 100 µm wide by about 20 µm deep. In some examples, the cross-sectional dimensions of the sub-channel may be about 100 µm wide by about 10 µm deep. In some examples, the cross-sectional dimensions of the sub-channel may be about 80 µm wide by about 100 µm deep. In some examples, the cross-sectional dimensions of the sub-channel may be about 60 µm wide by about 100 µm deep. In some examples, the cross-sectional dimensions of the sub-channel may be about 40 µm wide by about 100 µm deep. In some examples, the cross-sectional dimensions of the sub-channel may be about 20 µm wide by about 100 µm deep. In some examples, the cross-sectional dimensions of the sub-channel may be about 10 µm wide by about 100 µm deep. In some examples, the cross-sectional dimensions of the sub-channel may be about 80 µm wide by about 80 µm deep. In some examples, the cross-sectional dimensions of the sub-channel may be about 60 µm wide by about 60 µm deep. In some examples, the cross-sectional dimensions of the sub-channel may be about 40 µm wide by about 40 µm deep. In some examples, the cross-sectional dimensions of the sub-channel may be about 20 µm wide by about 20 µm deep. In some examples, the cross-sectional dimensions of the sub-channel may be about 10 µm wide by about 10 µm deep. The cross-sectional shape of the sub-channel may be any suitable cross-sectional shape including, but not limited to, circular, oval, triangular, square, or rectangular. In some embodiments, the cross sectional shape of the sub-channel is different than the cross-sectional shape of the microchannel. In some embodiments, the cross-sectional shape of the sub-channel is the same as the cross-sectional shape of the microchannel. The cross-sectional area of the sub-channel may be constant along the length of the sub-channel. Alternatively, or in addition to, the cross-sectional area of the sub-channel may vary along the length of the microchannel. The cross-sectional area of the sub-channel may vary between about 50% and 150%, between about 60% and 125%, between about 70% and 120%, between about 80% and 115%, between about 90% and 110%, between about 95% and 100%, or between about 98% and 102%. The cross-sectional area of the sub-channel may be less than or equal to about 10,000 µm², less than or equal to about 7,500 µm², less than or equal to about 5,000 µm², less than or equal to about 2,500 µm², less than or equal to about 1,000 µm², less than or equal to about 750 µm², less than or equal to about 500 µm², less than or equal to about 400 µm², less than or equal to about 300 µm², less than or equal to about 200 µm², less than or equal to about 100 µm², or less. In some embodiments, the cross-sectional area of the sub-channel is the same as the cross-sectional area of the microchannel. In some embodiments, the cross-sectional area of the sub-channel may be less than or equal to the area of the cross-sectional area of the microchannel. The cross-sectional area of the sub-channel may be less than or equal to about 98%, less than or equal to about 95%, less than or equal to about 90%, less than or equal to about 85%, less than or equal to about 80%, less than or equal to about 75%, less than or equal to about 70%, less than or equal to about 60%, less than or equal to about 50%, less than or equal to about 40%, less than or equal to about 30%, less than or equal to about 20%, less than or equal to about 20%, or less of the cross-sectional area of the microchannel.

In some embodiments, the lengths of the cross-channels are constant. In some embodiments, the lengths of the cross-channel may vary. The cross-channel may have a long dimension that is less than or equal to about 100 mm, less than or equal to about 75 mm, less than or equal to about 50 mm, less than or equal to about 40 mm, less than or equal to about 30 mm, less than or equal to about 20 mm, less than or equal to about 10 mm, less than or equal to about 8 mm, less than or equal to about 6 mm, less than or equal to about 4 mm, less than or equal to about 2 mm, or less. The length of the cross-channel may be bounded by the external length or width of the microfluidic device. In some embodiments, the cross-channel may have the same cross-sectional dimension as the microchannel. In some embodiments, the cross-channel may have a different cross-sectional dimension than the microchannel. In some embodiments, the cross-channel may have the same depth as the microchannel and a different cross-sectional dimension. In some embodiments, the cross-channel may have the same cross-sectional dimension as the microchannel and a different depth. For example, the cross-channel may have a depth of less than or equal to about 500 µm, less than or equal to about 250 µm, less than or equal to about 100 µm, less than or equal to about 80 µm, less than or equal to about 60 µm, less than or equal to about 30 µm, less than or equal to about 15 µm, or less. The cross-channel may have a cross-section width of less than or equal to about 500 µm, less than or equal to about 250 µm, less than or equal to about 100 µm, less than or equal to about 75 µm, less than or equal to about 50 µm, less than or equal to about 40 µm, less than or equal to about 30 µm, less than or equal to about 20 µm, less than or equal to about 10 µm, or less.

In some examples, the cross-sectional dimensions of the cross-channel may be about 100 µm wide by about 100 µm deep. In some examples, the cross-sectional dimensions of the cross-channel may be about 100 µm wide by about 80 µm deep. In some examples, the cross-sectional dimensions of the cross-channel may be about 100 µm wide by about 60 µm deep. In some examples, the cross-sectional dimensions of the cross-channel may be about 100 µm wide by about 40 µm deep. In some examples, the cross-sectional dimensions of the cross-channel may be about 100 µm wide by about 20 µm deep. In some examples, the cross-sectional dimensions of the cross-channel may be about 100 µm wide by about 10 µm deep. In some examples, the cross-sectional dimensions of the cross-channel may be about 80 µm wide by about 100 µm deep. In some examples, the cross-sectional dimensions of the cross-channel may be about 60 µm wide by about 100 µm deep. In some examples, the cross-sectional dimensions of the cross-channel may be about 40 µm wide by about 100 µm deep. In some examples, the cross-sectional dimensions of the cross-channel may be about 20 µm wide by about 100 µm deep. In some examples, the cross-sectional dimensions of the cross-channel may be about 10 µm wide by about 100 µm deep. In some examples, the cross-sectional dimensions of the cross-channel may be about 80 µm wide by about 80 µm deep. In some examples, the cross-sectional dimensions of the cross-channel may be about 60 µm wide by about 60 µm deep. In some examples, the cross-sectional dimensions of the cross-channel may be about 40 µm wide by about 40 µm deep. In some examples, the cross-sectional dimensions of the cross-channel may be about 20 µm wide by about 20 µm deep. In some examples, the cross-sectional dimensions of the cross-channel may be about 10 µm wide by about 10 µm deep.

The cross-sectional shape of the cross-channel may be any suitable cross-sectional shape including, but not limited to, circular, oval, triangular, square, or rectangular. In some embodiments, the cross sectional shape of the cross-channel is different than the cross-sectional shape of the microchannel. In some embodiments, the cross-sectional shape of the cross-channel is the same as the cross-sectional shape of the microchannel. The cross-sectional area of the cross-channel may be constant down the length of the cross-channel. Alternatively, or in addition to, the cross-sectional area of the cross-channel may vary down the length of the microchannel. The cross-sectional area of the cross-channel may vary between about 50% and 150%, between about 60% and 125%, between about 70% and 120%, between about 80% and 115%, between about 90% and 110%, between about 95% and 100%, or between about 98% and 102%. The cross-sectional area of the cross-channel may be less than or equal to about 10,000 µm$^2$, less than or equal to about 7,500 µm$^2$, less than or equal to about 5,000 µm$^2$, less than or equal to about 2,500 µm$^2$, less than or equal to about 1,000 µm$^2$, less than or equal to about 750 µm$^2$, less than or equal to about 500 µm$^2$, less than or equal to about 400 µm$^2$, less than or equal to about 300 µm$^2$, less than or equal to about 200 µm$^2$, less than or equal to about 100 µm$^2$, or less. In some embodiments, the cross-sectional area of the cross-channel is the same as the cross-sectional area of the microchannel. In some embodiments, the cross-sectional area of the cross-channel is less than the area of the cross-sectional area of the microchannel. The cross-sectional area of cross-channel may be less than or equal to about 98%, less than or equal to about 95%, less than or equal to about 90%, less than or equal to about 85%, less than or equal to about 80%, less than or equal to about 75%, less than or equal to about 70%, less than or equal to about 60%, less than or equal to about 50%, less than or equal to about 40%, less than or equal to about 30%, less than or equal to about 20%, less than or equal to about 20%, or less of the cross-sectional area of the microchannel.

Method for Fabricating a Microfluidic Device

In an aspect, the present disclosure provides methods for fabricating a microfluidic device. The method may comprise injection molding a thermoplastic to create a microfluidic structure. The microfluidic structure may comprise a microchannel, a plurality of microchambers, and a plurality of siphon apertures. The plurality of microchambers may be connected to the microchannel by the plurality of siphon apertures. The microchannel may comprise an inlet and an outlet. A thermoplastic thin film may be applied to cap the microfluidic structure. The thermoplastic thin film may be at least partially gas permeable when a pressure differential is applied across the thermoplastic thin film.

In some embodiments, the thermoplastic thin film is formed by injection molding. The thermoplastic thin film may be applied to the microfluidic structure by thermal bonding. Alternatively, or in addition to, the thin film may be applied by chemical bonding. In some embodiments, the thermoplastic thin film is formed as part of and during the injection molding process to form the microfluidic device.

The body of the microfluidic device and the thin film may comprise the same materials. Alternatively, the body of the microfluidic device and the thin film may comprise different materials. The body of the microfluidic device and the thin film may comprise a thermoplastic. Example thermoplastics include, but are not limited to, cyclo-olefin polymers, acrylic, acrylonitrile butadiene styrene, nylon, polylactic acid, polybenzimidazole, polycarbonate, polyether sulfone, poly ether ether ketone, polyetherimide, polyethylene, polyphenylene oxide, polyphenylene sulfide, polypropylene, polystyrene, polyvinyl chloride, polytetrafluoroethylene, polyester, polyurethane or any derivative thereof. The microfluidic device may comprise homopolymers, copolymers, or a combination thereof. The microfluidic device may be formed of inelastic materials. Alternatively or in addition to, the microfluidic device may be formed of elastic materials.

In an exemplary embodiment of the present disclosure, both the thermoplastic and the thin film are composed of a cyclo-olefin polymer. One suitable thermoplastic is ZEONOR® 1430R (Zeon Chemical, Japan) while one suitable thin film is ZEONOX® 1060R (Zeon Chemical, Japan). In some embodiments, the thin film is a material that is gas-impermeable at low pressure and at least partially gas permeable under pressure.

In some embodiments, the inlet and the outlet are formed by mechanical drilling. In some embodiments, the inlet and outlet are formed by melting, dissolving, or etching the thermoplastic.

Figure 4:
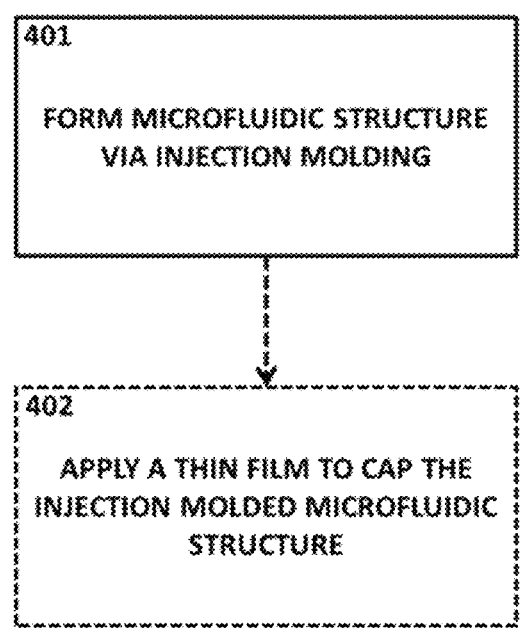
FIG. 4 schematically illustrates a method of manufacture of a microfluidic device.

FIG. 4 illustrates a method of manufacture of embodiments of the present disclosure. In FIG. 4, an injection molding process 401 is used to form a microfluidic structure. The microfluidic structure includes an array of microchambers, which are connected to at least one microchannel via siphon apertures, as shown in FIGS. 1A and 1B. The microfluidic structure is capped by a thin film. In the capping process, openings in at least one side of the microstructure are covered over in order to close and seal the microstructures. In some embodiments of the present disclosure, the capping is performed by a process 402 of applying a thin film to the injection molded microfluidic structure. In some embodiments of the present disclosure, the capping is performed by forming the thin film as part of the injection molding process 401.

As another example, while described in the context of a microstructure which is formed via injection molding, microfluidic devices formed by other microfabrication techniques may also benefit from the use of such a thin thermoplastic film to allow outgassing as described above. Such techniques include micromachining, microlithography, and hot embossing, as well as other microfabrication techniques.

Method of Analyzing a Nucleic Acid Sample

In an aspect, the present disclosure provides methods for using a microfluidic device to analyze a nucleic acid sample. The method may comprise providing a microfluidic device comprising a microchannel. The microchannel may comprise an inlet and an outlet. The microfluidic device may further comprise a plurality of microchambers connected to the microchannel by a plurality of siphon apertures. The microfluidic device may be sealed by a thermoplastic thin film disposed adjacent to a surface of the microfluidic device such that the thermoplastic thin film caps the microchannel, the plurality of microchambers, and the plurality of siphon apertures. A reagent may be applied to the inlet or the outlet. The microfluidic device may be filled by providing a first pressure differential between the reagent and the microfluidic device, causing the reagent to flow into the microfluidic device. The reagent may be partitioned into the microchambers by applying a second pressure differential between the microchannel and the plurality of microchambers to move the reagent into the plurality of microchambers and to force gas within the plurality of microchambers to pass through the thermoplastic thin film. The second pressure differential may be greater than the first pressure differential. A third pressure differential between the inlet and the outlet may be applied to introduce a fluid into the microchannel without introducing the fluid into the microchambers. The third pressure differential may be less than the second pressure differential.

In some embodiments, the inlet and the outlet are in fluid communication with a pneumatic pump. In some embodiments, the microfluidic device is in contact with a vacuum system. Filling and partitioning of a sample may be performed by applying pressure differentials across various features of the microfluidic device. In some embodiments, filling and partitioning of the sample may be performed without the use of valves between the microchambers and the microchannel to isolate the sample. For example, filling of the microchannel may be performed by applying a pressure differential between the sample to be loaded and the microchannel. This pressure differential may be achieved by pressurizing the sample or by applying vacuum to the microchannel. Filling the microchambers may be performed by applying a pressure differential between the microchannel and the microchambers. This may be achieved by pressurizing the microchannel or by applying a vacuum to the microchambers. Partitioning the sample may be performed by applying a pressure differential between a fluid and the microchannel. This pressure differential may be achieved by pressurizing the fluid or by applying a vacuum to the microchannel.

The thin film may employee different permeability characteristics under different applied pressure differentials. For example, the thin film may be gas impermeable at the first and third pressure differentials (e.g., low pressure), which may be smaller magnitude pressure differentials. The thin film may be at least partially gas permeable at the second pressure differential (e.g., high pressure), which may be a higher magnitude pressure differential. The first and third pressure differentials may be the same or they may be different. The first pressure differential may be the difference in pressure between the reagent in the inlet or outlet and the microfluidic device. During filling of the microfluidic device, the pressure of the reagent may be higher than the pressure of the microfluidic device. During filling of the microfluidic device, the pressure difference between the reagent and the microfluidic device (e.g., low pressure) may be less than or equal to about 8 pounds per square inch (psi), less than or equal to about 6 psi, less than or equal to about 4 psi, less than or equal to about 2 psi, less than or equal to about 1 psi, or less. In some examples, during filling of the microfluidic device, the pressure differential between the reagent and the microfluidic device may be from about 1 psi to about 8 psi. In some examples, during filling of the microfluidic device, the pressure differential between the reagent and the microfluidic device may be from about 1 psi to about 6 psi. In some examples, during filling of the microfluidic device, the pressure differential between the reagent and the microfluidic device may be from about 1 psi to about 4 psi. The microfluidic device may be filled by applying a pressure differential between the reagent and the microfluidic device for less than or equal to about 20 minutes, less than or equal to about 15 minutes, less than or equal to about 10 minutes, less than or equal to about 5 minutes, less than or equal to about 3 minutes, less than or equal to about 2 minutes, less than or equal about 1 minute, or less.

A filled microfluidic device may have reagent in the microchannel, siphon apertures, microchambers, or any combination thereof. Backfilling of the reagent into the microchambers may occur upon filling of the microfluidic device or may occur during application of a second pressure differential. The second pressure differential (e.g., high pressure) may correspond to the difference in pressure between the microchannel and the plurality of microchambers. During application of the second pressure differential a first fluid in the higher pressure domain may push a second fluid in the lower pressure domain through the thin film and out of the microfluidic device. The first and second fluids may comprise a liquid or a gas. The liquid may comprise an aqueous mixture or an oil mixture. The second pressure differential may be achieved by pressurizing the microchannel. Alternatively, or in addition to, the second pressure differentially may be achieved by applying a vacuum to the microchambers. During application of the second pressure differential, reagent in the microchannel may flow into the microchambers. Additionally, during the application of the second pressure differential gas trapped within the siphon apertures, microchambers, and microchannel may outgas through the thin film. During backfilling and outgassing of the microchambers, the pressure differential between the microchambers and the microchannel may be greater than or equal to about 6 psi, greater than or equal to about 8 psi, greater than or equal to about 10 psi, greater than or equal to about 12 psi, greater than or equal to about 14 psi, greater than or equal to about 16 psi, greater than or equal to about 18 psi, greater than or equal to about 20 psi, or greater. In some examples, during backfilling of the microchambers, the pressure differential between the microchambers and the microchannel is from about 8 psi to about 20 psi. In some examples, during backfilling of the microchambers, the pressure differential between the microchambers and the microchannel is from about 8 psi to about 18 psi. In some examples, during backfilling of the microchambers, the pressure differential between the microchambers and the microchannel is from about 8 psi to about 16 psi. In some examples, during backfilling of the microchambers, the pressure differential between the microchambers and the microchannel is from about 8 psi to about 14 psi. In some examples, during backfilling of the microchambers, the pressure differential between the microchambers and the microchannel is from about 8 psi to about 12 psi. In some examples, during backfilling of the microchambers, the pressure differential between the microchambers and the microchannel is from about 8 psi to about 10 psi. The microchambers may be backfilled and outgassed by applying a pressure differential for more than about 5 minutes, more than about 10 minutes, more than about 15 minutes, more than about 20 minutes, more than about 25 minutes, more than about 30 minutes, or more.

The sample may be partitioned by removing the excess sample from the microchannel. Removing excess sample from the microchannel may prevent reagents in one microchamber from diffusing through the siphon aperture into the microchannel and into other microchambers. Excess sample within the microchannel may be removed by introducing a fluid to the inlet or the outlet of the microchannel. The pressure of the fluid may be greater than the pressure of the microchannel, thereby creating a pressure differential between the fluid and the microchannel. The fluid may be oxygen, nitrogen, carbon dioxide, air, a noble gas, or any combination thereof. During partitioning of the sample, the pressure differential between the fluid and the microchannel may be less than or equal to about 8 psi, less than or equal to about 6 psi, less than or equal to about 4 psi, less than or equal to about 2 psi, less than or equal to about 1 psi, or less. In some examples, during partitioning of the sample, the pressure differential between the fluid and the microchannel may be from about 1 psi to about 8 psi. In some examples, during partitioning of the sample, the pressure differential between the fluid and the microchannel may be from about 1 psi to about 6 psi. In some examples, during partitioning of the sample, the pressure differential between the fluid and the microchannel may be from about 1 psi to about 4 psi. The sample may be partitioned by applying a pressure differential between the fluid and the microchannel for less than or equal to about 20 minutes, less than or equal to about 15 minutes, less than or equal to about 10 minutes, less than or equal to about 5 minutes, less than or equal to about 3 minutes, less than or equal to about 2 minutes, less than or equal to about 1 minute, or less.

FIGS. 3A-3D illustrate a method for use of the microfluidic device shown in FIG. 1A. In FIG. 3A, a low pressure is applied to reagent at the inlet 120 via a pneumatic pump 300 to force reagent into the microchannel 110 and thereby fill the microchambers via the siphon apertures. The pressure forces reagent to flow through the microchannel, and thereby to flow into the microchambers via the siphon apertures. At this time, gas bubbles such as bubble 301 may remain within the microchambers, siphon apertures, or microchannel. Filling via the application of low pressure may continue until the microchambers, siphon apertures, and microchannel are substantially filled with reagent. The reagent may be a reagent to be used in a polymerase chain reaction. In some embodiments, the reagent is diluted such that no more than one PCR template is present in the reagent per microchamber of the microfluidic device.

In FIG. 3B, the pneumatic pump 300 is connected to both inlets 120 and outlets 130 and a high pressure is applied. The high pressure is transmitted via the reagent and applied to gas bubbles such as bubble 301. Under the influence of this high pressure, thin film 150 becomes gas permeable, and the bubble 301 can outgas through the thin film 150. By applying this high pressure, the microchambers, siphon apertures, and microchannel can be rendered substantially free of gas bubbles, thereby avoiding fouling.

In FIG. 3C, fluid is reintroduced by applying low pressure to a gas at the inlet 120 via pneumatic pump 300. The air pressure may not be sufficient to allow the gas to outgas through the thin film or high enough to force gas bubbles into the siphon apertures and microchambers. Instead, the gas may clear the microchannel of reagent, leaving the reagent isolated in each microchamber and siphon aperture. In some embodiments, the gas is air. In some embodiments, the gas may be an inert gas such as nitrogen, carbon dioxide, or a noble gas. Such a gas may be used to avoid reaction between the reagent and the component gases of air.

FIG. 3D illustrates the state of the system after the low pressure has been applied in FIG. 3C. After application of the low pressure gas the microchambers and siphon apertures may remain filled with reagent, while the microchannel may be cleared of reagent. The reagent may remain stationary within the microchambers due to the capillary force and high surface tension created by the siphon aperture. The capillary force and high surface tension may prevent the reagent from flowing into the microchannel and minimize reagent evaporation.

Partitioning of the sample may be verified by the presence of an indicator within the reagent. An indicator may include a molecule comprising a detectable moiety. The detectable moiety may include radioactive species, fluorescent labels, chemiluminescent labels, enzymatic labels, colorimetric labels, or any combination thereof. Non-limiting examples of radioactive species include $^{3}$H, $^{14}$C, $^{22}$Na, $^{32}$P, $^{33}$P, $^{35}$S, $^{42}$K, $^{45}$Ca, $^{59}$Fe, $^{123}$I, $^{124}$I, $^{125}$I $^{131}$I, or $^{203}$Hg. Non-limiting examples of fluorescent labels include fluorescent proteins, optically active dyes (e.g., a fluorescent dye), organometallic fluorophores, or any combination thereof. Non-limiting examples of chemiluminescent labels include enzymes of the luciferase class such as Cypridina, *Gaussia, Renilla*, and Firefly luciferases. Non-limiting examples of enzymatic labels include horseradish peroxidase (HRP), alkaline phosphatase (AP), beta galactosidase, glucose oxidase, or other well-known labels.

In some embodiments, an indicator molecule is a fluorescent molecule. Fluorescent molecules may include fluorescent proteins, fluorescent dyes, and organometallic fluorophores. In some embodiments, the indicator molecule is a protein fluorophore. Protein fluorophores may include green fluorescent proteins (GFPs, fluorescent proteins that fluoresce in the green region of the spectrum, generally emitting light having a wavelength from 500-550 nanometers), cyan-fluorescent proteins (CFPs, fluorescent proteins that fluoresce in the cyan region of the spectrum, generally emitting light having a wavelength from 450-500 nanometers), red fluorescent proteins (RFPs, fluorescent proteins that fluoresce in the red region of the spectrum, generally emitting light having a wavelength from 600-650 nanometers). Non-limiting examples of protein fluorophores include mutants and spectral variants of AcGFP, AcGFP1, AmCyan, AmCyan1, AQ143, AsRed2, Azami Green, Azurite, BFP, Cerulean, CFP, CGFP, Citrine, copGFP, CyPet, dKeima-Tandem, DsRed, dsRed-Express, DsRed-Monomer, DsRed2, dTomato, dTomato-Tandem, EBFP, EBFP2, ECFP, EGFP, Emerald, EosFP, EYFP, GFP, HcRed-Tandem, HcRed1, JRed, Katuska, Kusabira Orange, Kusabira Orange2, mApple, mBanana, mCerulean, mCFP, mCherry, mCitrine, mECFP, mEmerald, mGrape1, mGrape2, mHoneydew, Midori-Ishi Cyan, mKeima, mKO, mOrange, mOrange2, mPlum, mRaspberry, mRFP1, mRuby, mStrawberry, mTagBFP, mTangerine, mTeal, mTomato, mTurquoise, mWasabi, PhiYFP, ReAsH, Sapphire, Superfolder GFP, T-Sapphire, TagCFP, TagGFP, TagRFP, TagRFP-T, TagYFP, tdTomato, Topaz, TurboGFP, Venus, YFP, YPet, ZsGreen, and ZsYellow1.

In some embodiments, the indicator molecule is a fluorescent dye. Non-limiting examples of fluorescent dyes include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, *lucifer* yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), 5- (or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-aminomethyl-coumarin, 7-Amino-4-methylcoumarin-3-acetic acid (AMCA), BODIPY fluorophores, 8-methoxypyrene-1, 3,6-trisulfonic acid trisodium salt, 3,6-Disulfonate-4-aminonaphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores.

In some embodiments, the indicator molecule is an organometallic fluorophore. Non limiting examples of organometallic fluorophores include lanthanide ion chelates, non-limiting examples of which include tris(dibenzoylmethane) mono(1,10-phenanthroline)europium(111), tris(dibenzoyl-methane) mono(5-amino-1,10-phenanthroline)europium (111), and Lumi4-Tb cryptate.

In some embodiments, the images are taken of the microfluidic device. Images may be taken of single microchambers, an array of microchambers, or of multiple arrays of microchambers concurrently. In some embodiments, the images are taken through the body of the microfluidic device. In some embodiments, images are taken through the thin film of the microfluidic device. In some embodiments, images are taken through both the body of the microfluidic device and through the thin film. In some embodiments, the body of the microfluidic device is substantially optically transparent. In some embodiments, the body of the microfluidic device is substantially optically opaque. In some embodiments, the thin film is substantially optically transparent. In some embodiments, images may be taken prior to filling the microfluidic device with reagent. In some embodiments, images may be taken after filling of the microfluidic device with reagent. In some embodiments, images may be taken during filling the microfluidic device with reagent. In some embodiments, images are taken to verify partitioning of the reagent. In some embodiments, images are taken during a reaction to monitor products of the reaction. In some embodiments, products of the reaction comprise amplification products. In some embodiments, images are taken at specified intervals. Alternatively, or in addition to, a video may be taken of the microfluidic device. The specified intervals may include taking an image at least every 300 seconds, at least every 240 seconds, at least every 180 seconds, at least every 120 seconds, at least every 90 seconds, at least every 60 seconds, at least every 30 seconds, at least every 15 seconds, at least every 10 seconds, at least every 5 seconds, at least every 4 seconds, at least every 3 seconds, at least every 2 seconds, at least every 1 second, or more frequently during a reaction.

In some embodiments, the method for using a microfluidic device may further comprise amplification of a nucleic acid sample. The microfluidic device may be filled with an amplification reagent comprising nucleic acid molecules, components necessary for an amplification reaction, an indicator molecule, and an amplification probe. The amplification may be performed by thermal cycling the plurality of microchambers. Detection of nucleic acid amplification may be performed by imaging the microchambers of the microfluidic device. The nucleic acid molecules may be quantified by counting the microchambers in which the nucleic acid molecules are successfully amplified and applying Poisson statistics. In some embodiments, nucleic acid amplification and quantification may be performed in a single integrated unit.

A variety of nucleic acid amplification reactions may be used to amplify the nucleic acid molecule in a sample to generate an amplified product. Amplification of a nucleic acid target may be linear, exponential, or a combination thereof. Non-limiting examples of nucleic acid amplification methods include primer extension, polymerase chain reaction, reverse transcription, isothermal amplification, ligase chain reaction, helicase-dependent amplification, asymmetric amplification, rolling circle amplification, and multiple displacement amplification. In some embodiments, the amplification product is DNA or RNA. For embodiments directed towards DNA amplification, any DNA amplification method may be employed. DNA amplification methods include, but are not limited to, PCR, real-time PCR, assembly PCR, asymmetric PCR, digital PCR, dial-out PCR, helicase-dependent PCR, nested PCR, hot start PCR, inverse PCR, methylation-specific PCR, miniprimer PCR, multiplex PCR, overlap-extension PCR, thermal asymmetric interlaced PCR, touchdown PCR, and ligase chain reaction. In some embodiments, DNA amplification is linear, exponential, or any combination thereof. In some embodiments, DNA amplification is achieved with digital PCR (dPCR).

Reagents necessary for nucleic acid amplification may include polymerizing enzymes, reverse primers, forward primers, and amplification probes. Examples of polymerizing enzymes include, without limitation, nucleic acid polymerase, transcriptase, or ligase (i.e., enzymes which catalyze the formation of a bond). The polymerizing enzyme can be naturally occurring or synthesized. Examples of polymerases include a DNA polymerase, and RNA polymerase, a thermostable polymerase, a wild-type polymerase, a modified polymerase, *E. coli* DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. For a Hot Start polymerase, a denaturation step at a temperature from about 92° C. to 95° C. for a time period from about 2 minutes to 10 minutes may be required.

In some embodiments, the amplification probe is a sequence-specific oligonucleotide probe. The amplification probe may be optically active when hybridized with an amplification product. In some embodiments, the amplification probe is only detectable as nucleic acid amplification progresses. The intensity of the optical signal may be proportional to the amount of amplified product. A probe may be linked to any of the optically-active detectable moieties (e.g., dyes) described herein and may also include a quencher capable of blocking the optical activity of an associated dye. Non-limiting examples of probes that may be useful as detectable moieties include TAQMAN® probes, TAQMAN® Tamara probes, TAQMAN® MGB probes, Lion probes, locked nucleic acid probes, or molecular beacons. Non-limiting examples of quenchers that may be useful in blocking the optical activity of the probe include BLACK HOLE QUENCHERS® (BHQ), IOWA BLACK® FQ and RQ quenchers, or Internal ZEN® Quenchers. Alternatively or in addition to, the probe or quencher may be any known probe that is useful in the context of the methods of the present disclosure.

In some embodiments, the amplification probe is a dual labeled fluorescent probe. The dual labeled probe may include a fluorescent reporter and a fluorescent quencher linked with a nucleic acid. The fluorescent reporter and fluorescent quencher may be positioned in close proximity to each other. The close proximity of the fluorescent reporter and fluorescent quencher may block the optical activity of the fluorescent reporter. The dual labeled probe may bind to the nucleic acid molecule to be amplified. During amplification, the fluorescent reporter and fluorescent quencher may be cleaved by the exonuclease activity of the polymerase. Cleaving the fluorescent reporter and quencher from the amplification probe may cause the fluorescent reporter to regain its optical activity and enable detection. The dual labeled fluorescent probe may include a 5' fluorescent reporter with an excitation wavelength maximum of about 450 nanometers (nm), 500 nm, 525 nm, 550 nm, 575 nm, 600 nm, 625 nm, 650 nm, 675 nm, 700 nm, or higher and an emission wavelength maximum of about 500 nm, 525 nm, 550 nm, 575 nm, 600 nm, 625 nm, 650 nm, 675 nm, 700 nm, or higher. The dual labeled fluorescent probe may also include a 3' fluorescent quencher. The fluorescent quencher may quench fluorescent emission wavelengths between about 380 nm and 550 nm, 390 nm and 625 nm, 470 nm and 560 nm, 480 nm and 580 nm, 550 nm and 650 nm, 550 nm and 750 nm, or 620 nm and 730 nm.

In some embodiments, the nucleic acid amplification is performed by thermal cycling the microchambers of the microfluidic device. Thermal cycling may include controlling the temperature of the microfluidic device by applying heating or cooling to the microfluidic device. Heating or cooling methods may include resistive heating or cooling, radiative heating or cooling, conductive heating or cooling, convective heating or cooling, or any combination thereof. Thermal cycling may include cycles of incubating the microchambers at a temperature sufficiently high to denature nucleic acid molecules for a duration followed by incubation of the microchambers at an extension temperature for an extension duration. Denaturation temperatures may vary depending upon, for example, the particular nucleic acid sample, the reagents used, and the desired reaction conditions. In some embodiments, a denaturation temperature may be from about 80° C. to about 110° C. In some embodiments, a denaturation temperature may be from about 85° C. to about 105° C. In some embodiments, a denaturation temperature may be from about 90° C. to about 100° C. In some embodiments, a denaturation temperature may be from about 90° C. to about 98° C. In some embodiments, a denaturation temperature may be from about 92° C. to about 95° C. In some embodiments, a denaturation temperature may be at least about 80° C., at least about 81° C., at least about 82° C., at least about 83° C., at least about 84° C., at least about 85° C., at least about 86° C., at least about 87° C., at least about 88° C., at least about 89° C., at least about 90° C., at least about 91° C., at least about 92° C., at least about 93° C., at least about 94° C., at least about 95° C., at least about 96° C., at least about 97° C., at least about 98° C., at least about 99° C., at least about 100° C., or higher.

The duration for denaturation may vary depending upon, for example, the particular nucleic acid sample, the reagents used, and the desired reaction conditions. In some embodiments, the duration for denaturation may be less than or equal to about 300 seconds, 240 seconds, 180 seconds, 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second. In an alternative embodiment, the duration for denaturation may be no more than about 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second.

Extension temperatures may vary depending upon, for example, the particular nucleic acid sample, the reagents used, and the desired reaction conditions. In some embodiments, an extension temperature may be from about 30° C. to about 80° C. In some embodiments, an extension temperature may be from about 35° C. to about 75° C. In some embodiments, an extension temperature may be from about 45° C. to about 65° C. In some embodiments, an extension temperature may be from about 55° C. to about 65° C. In some embodiments, an extension temperature may be from about 40° C. to about 60° C. In some embodiments, an extension temperature may be at least about 35° C., at least about 36° C., at least about 37° C., at least about 38° C., at least about 39° C., at least about 40° C., at least about 41° C., at least about 42° C., at least about 43° C., at least about 44° C., at least about 45° C., at least about 46° C., at least about 47° C., at least about 48° C., at least about 49° C., at least about 50° C., at least about 51° C., at least about 52° C., at least about 53° C., at least about 54° C., at least about 55° C., at least about 56° C., at least about 57° C., at least about 58° C., at least about 59° C., at least about 60° C., at least about 61° C., at least about 62° C., at least about 63° C., at least about 64° C., at least about 65° C., at least about 66° C., at least about 67° C., at least about 68° C., at least about 69° C., at least about 70° C., at least about 71° C., at least about 72° C., at least about 73° C., at least about 74° C., at least about 75° C., at least about 76° C., at least about 77° C., at least about 78° C., at least about 79° C., or at least about 80° C.

Extension time may vary depending upon, for example, the particular nucleic acid sample, the reagents used, and the desired reaction conditions. In some embodiments, the duration for extension may be less than or equal to about 300 seconds, 240 seconds, 180 seconds, 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second. In an alternative embodiment, the duration for extension may be no more than about 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second.

Nucleic acid amplification may include multiple cycles of thermal cycling. Any suitable number of cycles may be performed. In some embodiments, the number of cycles performed may be more than about 5, more than about 10, more than about 15, more than about 20, more than about 30, more than about 40, more than about 50, more than about 60, more than about 70, more than about 80, more than about 90, more than about 100 cycles, or more. The number of cycles performed may depend upon the number of cycles necessary to obtain detectable amplification products. For example, the number of cycles necessary to detect nucleic acid amplification during dPCR may be less than or equal to about 100, less than or equal to about 90, less than or equal to about 80, less than or equal to about 70, less than or equal to about 60, less than or equal to about 50, less than or equal to about 40, less than or equal to about 30, less than or equal to about 20, less than or equal to about 15, less than or equal to about 10, less than or equal to about 5 cycles, or less.

The time to reach a detectable amount of amplification product may vary depending upon the particular nucleic acid sample, the reagents used, the amplification reaction used, the number of amplification cycles used, and the desired reaction conditions. In some embodiments, the time to reach a detectable amount of amplification product may be about 120 minutes or less, 90 minutes or less, 60 minutes or less, 50 minutes or less, 40 minutes or less, 30 minutes or less, 20 minutes or less, 10 minutes or less, or 5 minutes or less.

In some embodiments, the ramping rate (i.e., the rate at which the microchamber transitions from one temperature to another) is important for amplification. For example, the temperature and time for which an amplification reaction yields a detectable amount of amplified product may vary depending upon the ramping rate. The ramping rate may impact the time(s), temperature(s), or both the time(s) and temperature(s) used during amplification. In some embodiments, the ramping rate is constant between cycles. In some embodiments, the ramping rate varies between cycles. The ramping rate may be adjusted based on the sample being processed. For example, optimum ramping rate(s) may be selected to provide a robust and efficient amplification method.

Figure 5:
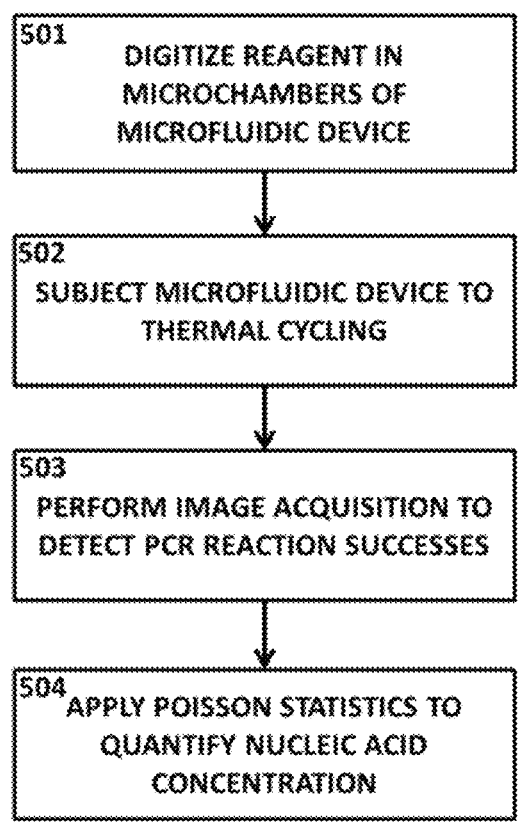
FIG. 5 schematically illustrates an exemplary digital PCR process to be employed with the a microfluidic device.

FIG. 5 illustrates a digital PCR process to be employed with the above-described microfluidic device. In step 501, reagent is partitioned as shown in FIGS. 3A-3D. In step 502, the reagent is subjected to thermal cycling to run the PCR reaction on the reagent in the microchambers. This step may be performed, for example, using a flat block thermal cycler. In step 503, image acquisition is performed to determine which microchambers have successfully run the PCR reaction. Image acquisition may, for example, be performed using a three color probe detection unit. In step 504, Poisson statistics are applied to the count of microchambers determined in step 503 to convert the raw number of positive chambers into a nucleic acid concentration.

System for Analyzing a Nucleic Acid Sample

In an aspect, the present disclosure provides an apparatus for using a microfluidic device to analyze nucleic acid samples. The apparatus may comprise a transfer stage configured to hold one or more microfluidic devices. The microfluidic devices may comprise a microchannel with an inlet and an outlet, a plurality of microchambers connected to the microchannel by a plurality of siphon apertures, and a thin film capping or covering the microfluidic device. The apparatus may comprise a pneumatic module in fluid communication with the microfluidic device. The pneumatic module may load reagent into the microfluidic device and partition the reagent into the microchambers. The apparatus may comprise a thermal module in thermal communication with the plurality of microchambers. The thermal module may control the temperature of the microchambers and thermal cycle the microchambers. The apparatus may comprise an optical module capable of imaging the plurality of microchambers. The apparatus may also comprise a computer processor coupled to the transfer stage, pneumatic module, thermal module, and optical module. The computer processor may be programmed to (i) direct the pneumatic module to load reagent into the microfluidic device and partition the reagent into the plurality of microchambers, (ii) direct the thermal module to thermal cycle the plurality of microchambers, and (iii) direct the optical module to image the plurality of microchambers.

The transfer stage may be configured input the microfluidic device, hold the microfluidic device, and output the microfluidic device. The transfer stage may be stationary in one or more coordinates. Alternatively, or in addition to, the transfer stage may be capable of moving in the X-direction, Y-direction, Z-direction, or any combination thereof. The transfer stage may be capable of holding a single microfluidic device. Alternatively, or in addition to, the transfer stage may be capable of holding at least 2, at least 3, at least 4, at least 5, at least 6, at least 7, at least 8, at least 9, at least 10, or more microfluidic devices.

The pneumatic module may be configured to be in fluid communication with the inlets and the outlets of the microfluidic device. The pneumatic module may have multiple connection points capable of connecting to multiple inlets and multiple outlets. The pneumatic module may be able to fill, backfill, and partition a single array of microchambers at a time or multiple arrays of microchambers in tandem. The pneumatic module may further comprise a vacuum module. The pneumatic module may provide increased pressure to the microfluidic device or provide vacuum to the microfluidic device.

The thermal module may be configured to be in thermal communication with the microchambers of the microfluidic devices. The thermal module may be configured to control the temperature of a single array of microchambers or to control the temperature of multiple arrays of microchambers. The thermal control module may perform the same thermal program across all arrays of microchambers or may perform different thermal programs with different arrays of microchambers.

The optical module may be configured to emit and detect multiple wavelengths of light. Emission wavelengths may correspond to the excitation wavelengths of the indicator and amplification probes used. The emitted light may include wavelengths with a maximum intensity around about 450 nm, 500 nm, 525 nm, 550 nm, 575 nm, 600 nm, 625 nm, 650 nm, 675 nm, 700 nm, or any combination thereof. Detected light may include wavelengths with a maximum intensity around about 500 nm, 525 nm, 550 nm, 575 nm, 600 nm, 625 nm, 650 nm, 675 nm, 700 nm, or any combination thereof. The optical module may be configured to emit one, two, three, four, or more wavelengths of light. The optical module may be configured to detect one, two, three, four, or more wavelengths of light. On emitted wavelength of light may correspond to the excitation wavelength of indicator molecule. Another emitted wavelength of light may correspond to the excitation wavelength of the amplification probe. One detected wavelength of light may correspond to the emission wavelength of an indicator molecule. Another detected wavelength of light may correspond to an amplification probe used to detect a reaction within the microchambers. The optical module may be configured to image sections of an array of microchambers. Alternatively, or in addition to, the optical module may image an entire array of microchambers in a single image.

Figure 6:
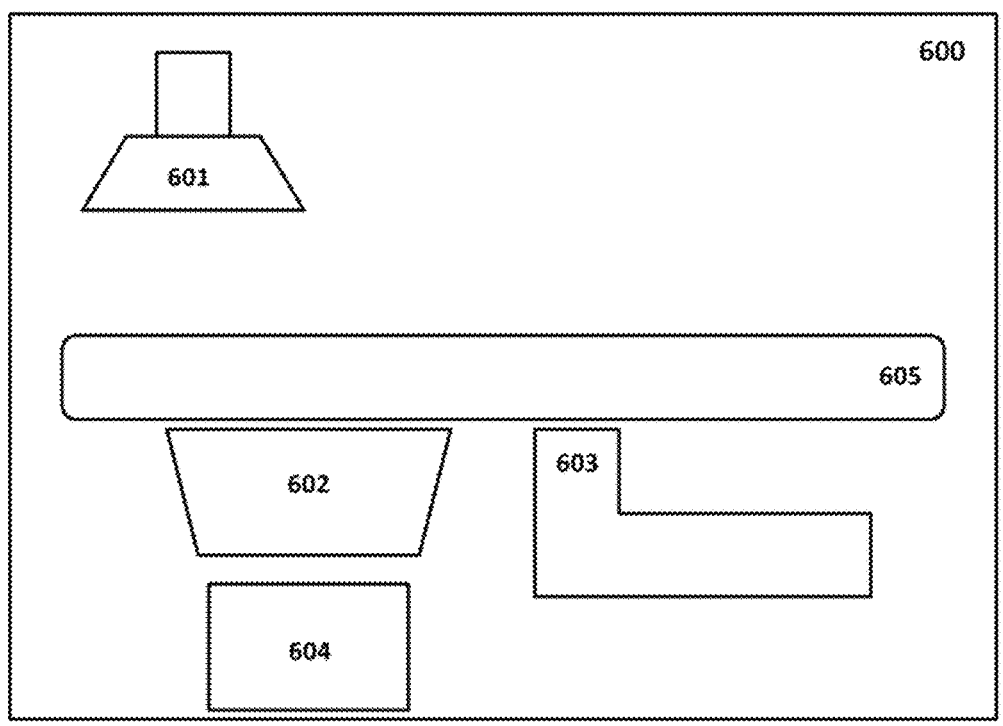
FIG. 6 schematically illustrates a machine for performing the a nucleic acid amplification and quantification method in a single machine.

FIG. 6 illustrates a machine 600 for performing the process of FIG. 5 in a single machine. The machine 600 includes a pneumatic module 601, which contains pumps and manifolds and may be moved in a Z-direction, operable to perform the application of pressure as described in FIGS. 3A-3D. Machine 600 also includes a thermal module 602, such as a flat block thermal cycler, to thermally cycle the microfluidic device and thereby cause the polymerase chain reaction to run. Machine 600 further includes an optical module 603, such as an epi-fluorescent optical module, which can optically determine which microchambers in the microfluidic device have successfully run the PCR reaction. The optical module 603 may feed this information to a processor 604, which uses Poisson statistics to convert the raw count of successful microchambers into a nucleic acid concentration. A transfer stage 605 may be used to move a given microfluidic device between the various modules and to handle multiple microfluidic devices simultaneously. The microfluidic device described above, combined with the incorporation of this functionality into a single machine, reduces the cost, workflow complexity, and space requirements for dPCR over other implementations of dPCR.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings.

For example, while described in the context of a dPCR application, other microfluidic devices which may require a number of isolated microchambers filled with a liquid, that are isolated via a gas or other fluid, may benefit from the use of a thin thermoplastic film to allow outgassing to avoid gas fouling while also providing an advantage with respect to manufacturability and cost. Other than PCR, other nucleic acid amplification methods such as loop mediated isothermal amplification can be adapted to perform digital detection of specific nucleic acid sequences according to embodiments of the present disclosure. The microchambers can also be used to isolate single cells with the siphoning apertures designed to be close to the diameter of the cells to be isolated. In some embodiments, when the siphoning apertures are much smaller than the size of blood cells, embodiments of the present disclosure can be used to separate blood plasma from whole blood.

Computer Systems for Analyzing a Nucleic Acid Sample

Figure 7:
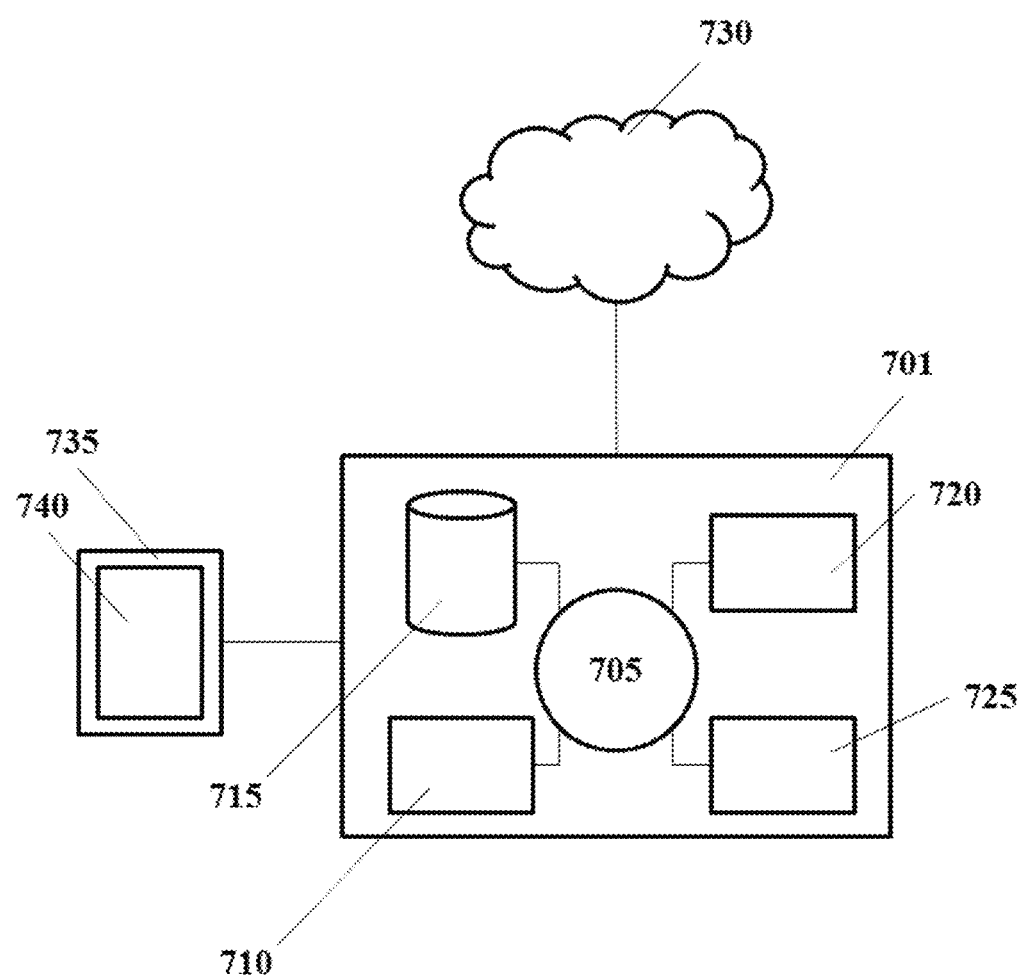
FIG. 7 schematically illustrates an example computer control system that is programmed or otherwise configured to implement methods provided herein.

The present disclosure provides computer control systems that are programmed to implement methods of the disclosure. FIG. 7 shows a computer system 701 that can be programmed or otherwise configured for nucleic acid sample processing and analysis, including sample partitioning, amplification, and detection. The computer system 701 can regulate various aspects of methods and systems of the present disclosure. The computer system 701 can be an electronic device of a user or a computer system that can be remotely located with respect to the electronic device. The electronic device can be a mobile electronic device.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that can be in communication with the Internet. The network 730 in some cases can be a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user (e.g., service provider). Examples of remote computer systems include personal computers (e.g., portable PC), slate or tablet PC's (e.g., iPad, SAMSUNG® Galaxy Tab), telephones, Smart phones (e.g., APPLE® iPhone, Android-enabled device, BLACKBERRY®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

In one aspect, the present disclosure provides a non-transitory computer-readable medium comprising machine executable code that, upon execution by one or more computer processors, implements a method for forming a microfluidic device to amplify and quantify a nucleic acid sample. The method may comprise: injection molding thermoplastic to create a microfluidic structure comprising at least one microchannel, a plurality of microchambers, and a plurality of siphon apertures, wherein the plurality of microchambers are connected to the at least one microchannel by the plurality of siphon apertures; forming at least one inlet and at least one outlet, wherein the at least one inlet and the at least one outlet are in fluid communication with the at least on microchannel; and applying a thermoplastic thin film to cap the microfluidic structure, wherein the thermoplastic thin film is at least partially gas permeable to a pressure differential is applied across the thermoplastic thin film.

In one aspect, the present disclosure provides a non-transitory computer-readable medium comprising machine executable code that, upon execution by one or more computer processors, implements a method for analyzing and quantifying a nucleic acid sample. The method may comprise: providing the microfluidic device comprising at least one microchannel, wherein the at least one microchannel comprises at least one inlet and at least one outlet, and wherein the microfluidic device further comprises a plurality of microchambers connected to the microchannel by a plurality of siphon apertures, and a thermoplastic thin film disposed adjacent to a surface of the microfluidic device such that the thermoplastic thin film caps the microchannel, the plurality of microchambers, and the plurality of siphon apertures; providing a reagent to the at least one inlet or to the at least one outlet; filling the microfluidic device by providing a first pressure differential between the reagent and the microfluidic device, wherein the first pressure differential causes the reagent to flow into the microfluidic device; applying a second pressure differential between the microchannel and the plurality of microchambers to move the reagent into the plurality of microchambers and to force gas within the plurality of microchambers to pass through the thermoplastic thin film capping or covering the plurality of microchambers, the plurality of siphon apertures, and the microchannel, wherein the second pressure differential is greater than the first pressure differential; and applying a third pressure differential between the at least one inlet and the at least one outlet to introduce a fluid into the microchannel without introducing the fluid into the microchambers, wherein the third pressure differential is less than second pressure differential.

Aspects of the systems and methods provided herein, such as the computer system 701, can be embodied in programming Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, for example, depth profile of an epithelial tissue. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 705. The algorithm can, for example, regulate systems or implement methods provided herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLE 1

Demonstration of Reagent Partitioning

Figure 8A:
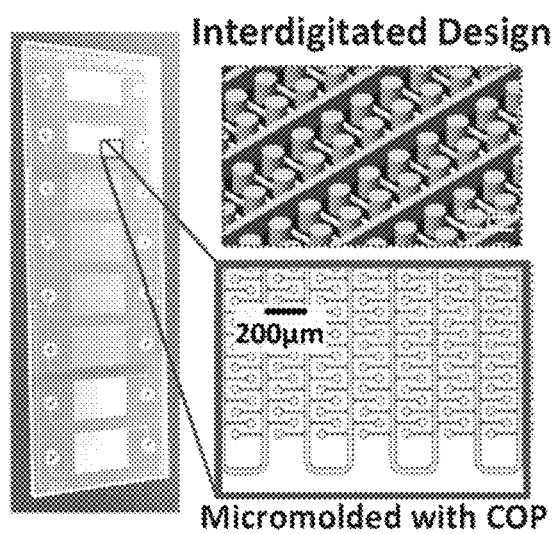
FIGS. 8A and 8B show the microfluidic device and sample partitioning.

Reagent partitioning is demonstrated using a microfluidic device fabricated using standard microscope slide dimensions. The total dimensions of the microfluidic device are 1 inch wide, 3 inches long, and 0.6 inches thick. The device contains four different microchamber array designs and a total of eight different arrays of microchambers. FIG. 8A shows the eight-unit device and an enlarged perspective of one of the four array designs. The microfluidic device is molded from a cyclo-olefin polymer (COP), ZEONOR® 790R (Zeon Chemicals, Japan) and sealed by thermal bonding with a 100 μm COP thin film, ZEONOX® ZF14 (Zeon Chemicals, Japan). The shown enlarged microfluidic segment has a serpentine microchannel connected to microchambers by siphon apertures. The microchambers are in a gridded configuration. The microchambers and microchannel have a depth of 40 μm the siphon apertures have a depth of 10 μm. Each isolated microfluidic segment has an inlet and an outlet channel. The inlet and outlet channels are mechanically drilled before the film is thermally bonded to the base of the microfluidic device. The inlet and outlet channels are 1.6 mm in diameter.

Figure 8B:
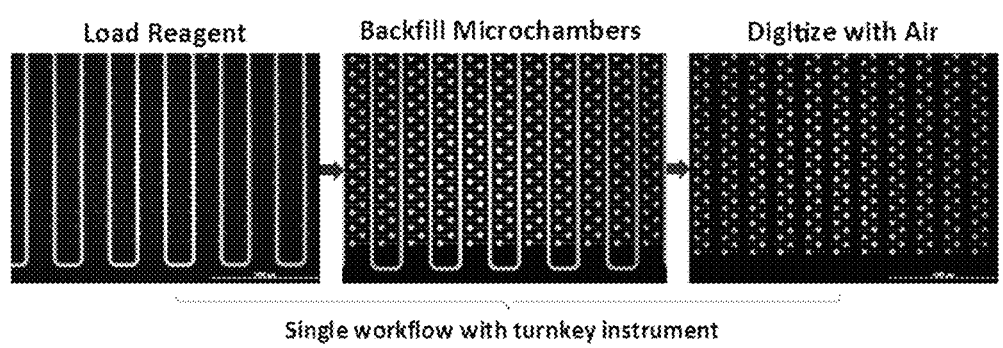

FIG. 8B shows fluorescent images of reagent loading, microchamber backfilling, and partitioning. Prior to loading the microfluidic device 2 microliters (μL) of a 4 kiloDalton (kDa) fluorescein conjugated dextran (Sigma-Aldrich, St. Louis, Mo.) is pipetted into the inlet. The microfluidic device is then contacted with a pneumatic controller. The pneumatic controller loads the microchannel of the microfluidic device by applying 4 psi of pressure to the inlet for 3 minutes. The microchambers are filled by pressurizing both the inlet and the outlet to 10 psi for 20 minutes. The reagent is then partitioned by flowing air at 4 psi from the inlet of the microfluidic device to clear reagent from the microchannel.

EXAMPLE 2

Single Instrument Workflow for dPCR

Figure 9:
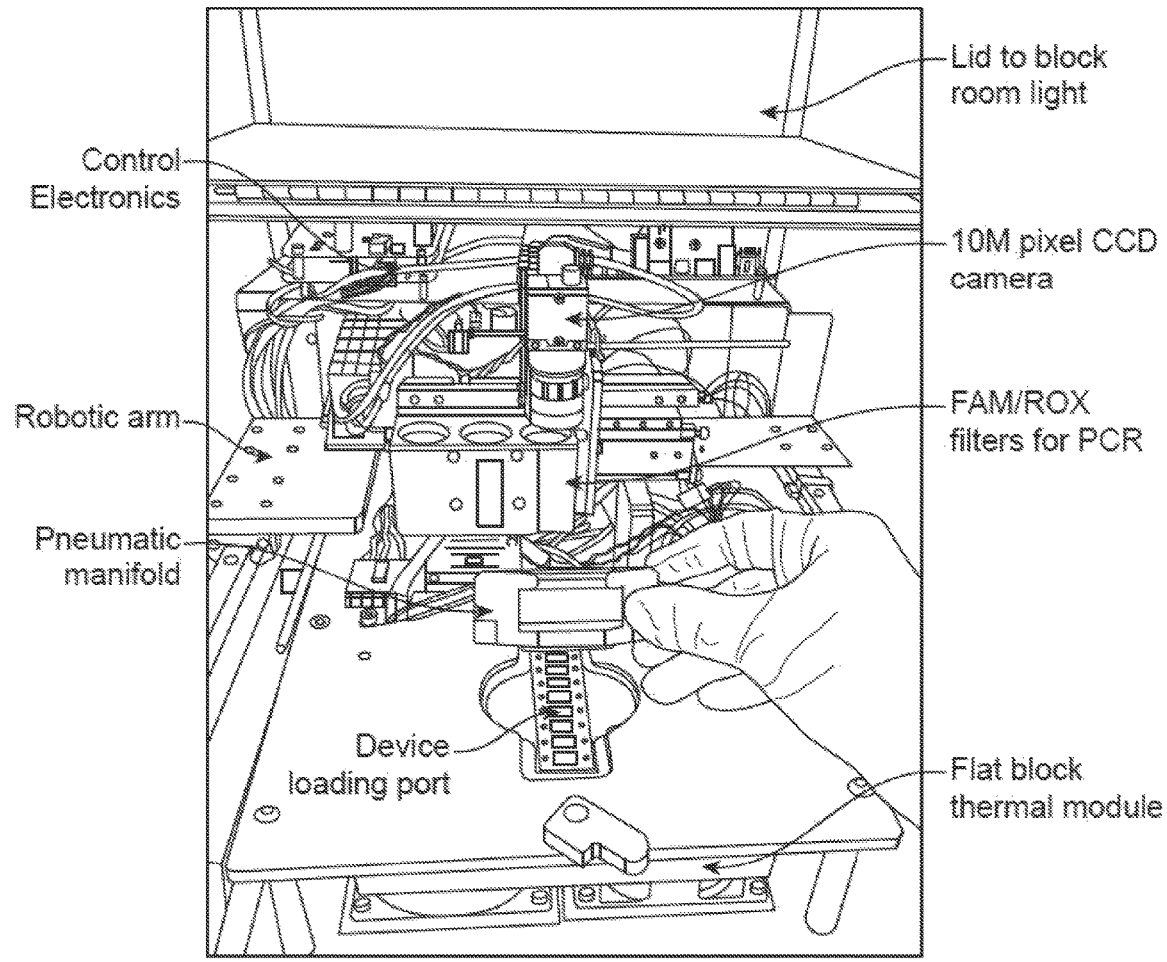
FIG. 9 shows an example system for processing a nucleic acid sample.

The methods for amplification and quantification of nucleic acids in the microfluidic device may be performed in a single instrument. The instrument may be capable of reagent partitioning, thermal cycling, image acquisition, and data analysis. FIG. 9 shows a prototype instrument capable of a single instrument work flow. The instrument is designed to accommodate up to four devices at a time and enable concurrent image acquisition and thermal cycling. The instrument contains a pneumatic module for reagent partitioning, a thermal module for temperature control and thermal cycling, an optical module for imaging, and a scanning module. The optical module has two fluorescent imaging capabilities and is able to detect fluorescent emissions of approximately 520 nm and 600 nm, which correspond to the emission wavelengths of FAM and ROX fluorophores, respectively. The optical module has a 25 mm by 25 mm field of view and a Numerical Aperture (NA) of 0.14.

Figure 10A:
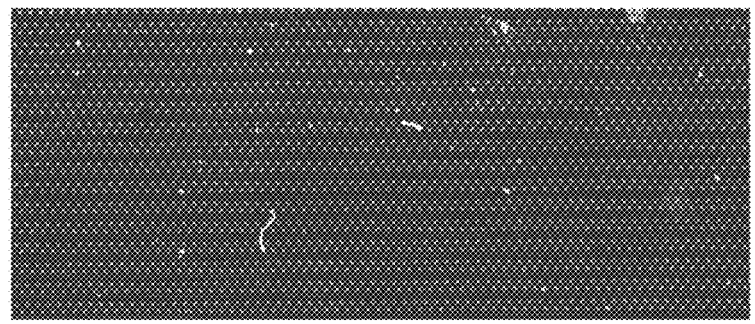
FIGS. 10A-10D show two color (one color representing sample signal and the other representing a normalization signal) fluorescent detection of nucleic acid amplification of partitions containing approximately one nucleic acid template copy on average and partitions containing zero nucleic acid template copies (no template control or NTC)
Figure 10B:
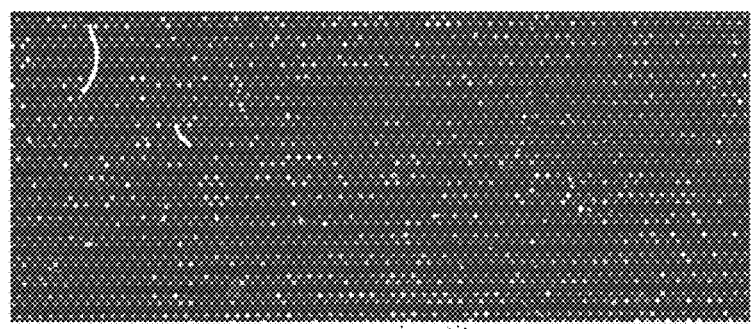
Figure 10C:
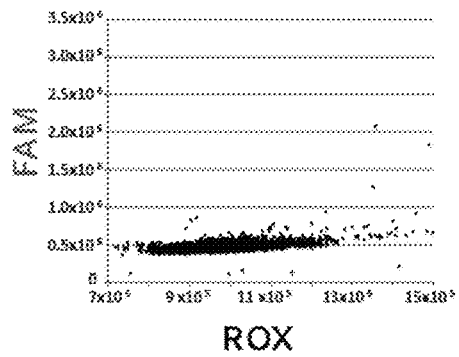
Figure 10D:
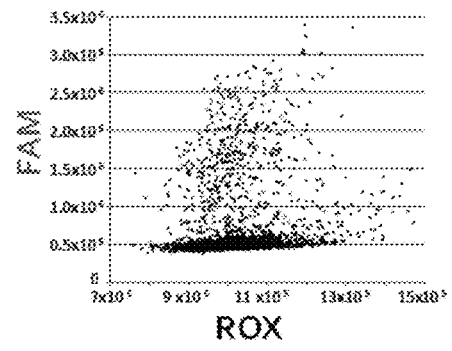

The single instrument workflow may be tested using a well-established qPCR assay utilizing a TaqMan probe as a reporter. Briefly, a nucleic acid sample is mixed with PCR reagents. The PCR reagents include forward primers, reverse primers, TaqMan probes, and a ROX indicator. The sequence of the forward primer is 5'-GCC TCA ATA AAG CTT GCC TTG A-3' (SEQ ID NO: 1). The sequence of the reverse primer is 5'-GGG GCG CAC TGC TAG AGA-3' (SEQ ID NO: 2). The sequence of the TaqMan probe is 5'-[FAM]-CCA GAG TCA CAC AAC AGA CGG GCA CA-[BHQ1]-3' (SEQ ID NO: 3). The nucleic acid sample and PCR reagents are loaded and partitioned within the microfluidic device following the above mentioned protocol. PCR amplification is performed by increasing the temperature of the microchambers to 95° C. and holding the temperature for 10 minutes followed by forty cycles ramping the temperature of the microchambers from 95° C. to 59° C. at a rate of 2.4° C. per second with a 1 minute hold at 59° C. prior to returning the temperature to 95° C. FIGS. 10A-10D show fluorescent images of samples containing approximately one nucleic acid template copy per partition and partitions containing zero nucleic acid template copies per partition (no template control or NTC) after PCR amplification and fluorescence intensity plots of samples containing approximately one nucleic acid copy per partition and NTC partitions after PCR amplification. FIG. 10A shows a fluorescent image of the partitioned sample containing no nucleic acid template and each grey dot represents a single microchamber containing the PCR reagents. The image is taken by exciting the ROX indicator within each microchamber with approximately 575 nm light and imaging the emission spectrum, which has a max emission at approximately 600 nm. FIG. 10B shows the partitioned sample containing approximately one nucleic acid template copy per partition after PCR amplification. After PCR amplification, imaging shows microchambers that contain the ROX indicator and microchambers that contain both the ROX indicator and emission from the FAM probe. The FAM probe has an excitation wavelength of approximately 495 nm and an emission wavelength maximum of approximately 520 nm. Individual microchambers contain the ROX indicator, the FAM probe, and the BHQ-1 quencher. As with FIG. 10A each grey dot represents a microchamber containing the partitioned sample with no nucleic acid template. The white dots represent microchambers that contain nucleic acid samples that have been successfully amplified. Upon successful PCR amplification, the FAM fluorophore and BHQ-1 quencher may be cleaved from the TaqMan probe, resulting in a detectable fluorescent signal. FIGS. 10C and 10D show a 2-dimensional scatter plot of the FAM fluorescent intensity as a function of the ROX fluorescent intensity for each microchamber for the partitioned and amplified microfluidic device, respectively. FIG. 10C shows a sample containing zero nucleic acid templates per partition, resulting in a FAM fluorescent intensity that is predominantly constant over a range of ROX fluorescent intensities. FIG. 10D shows a sample containing approximately one nucleic acid template copy per partition, resulting in a FAM fluorescent intensity that varies as a function of ROX fluorescent intensity due to the presence of amplification signals within the partition.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A device for processing a biological sample, comprising:
a plurality of chambers configured to retain said biological sample during processing; and
at least one gas permeable film or membrane covering said plurality of chambers, wherein said at least one gas permeable film or membrane is configured to permit gas flow from a chamber of said plurality of chambers to a location external to said chamber.

2. The device of claim 1, wherein said at least one gas permeable film or membrane is a plurality of gas permeable films or membranes, and wherein said chamber is covered by a gas permeable film or membrane of said plurality of gas permeable films or membranes.

3. The device of claim 1, wherein said at least one gas permeable film or membrane seals said plurality of chambers.

4. The device of claim 1, further comprising a fluid flow path in fluid communication with said plurality of chambers, wherein said fluid flow path is configured to provide reagents to said plurality of chambers.

5. The device of claim 4, further comprising a plurality of siphon apertures in fluid communication with said fluid flow path and said plurality of chambers, wherein said plurality of siphon apertures is configured to provide reagents from said fluid flow path to said plurality of chambers.

6. The device of claim 1, wherein said at least one gas permeable film or membrane comprises a polymer.

7. The device of claim 1, wherein said at least one gas permeable film or membrane has a thickness of at most about 100 micrometers.

8. The device of claim 1, wherein said at least one gas permeable film or membrane has a thickness of less than or equal to about 50 micrometers.

9. The device of claim 1, wherein said at least one gas permeable film or membrane is configured to permit gas flow therethrough upon application of a pressure differential in excess of a threshold.

10. The device of claim 1, wherein said at least one gas permeable film or membrane is configured to be impermeable to water.

11. A device for processing a biological sample, comprising a plurality of chambers configured to retain said biological sample during processing, wherein a chamber of said plurality of chambers comprises a barrier that is configured to permit gas flow from a chamber of said plurality of chambers to a location external to said chamber.

12. The device of claim 11, wherein said barrier is a gas permeable film or membrane.

13. The device of claim 11, further comprising a fluid flow path in fluid communication with said plurality of chambers, wherein said fluid flow channel is configured to provide reagents to said plurality of chambers.

14. The device of claim 11, wherein said barrier has a thickness of at most about 100 micrometers.

15. The device of claim 11, wherein said barrier has a thickness of less than or equal to about 50 micrometers.

16. The device of claim 11, wherein said chamber comprises a plurality of barriers, and wherein said barrier is separable from one or more other barriers of said plurality of barriers.

17. The device of claim 11, wherein said barrier comprises a polymer.

18. The device of claim 11, wherein said barrier is configured to be impermeable to water.

19. The device of claim 11, wherein said barrier is configured to permit gas flow therethrough upon application of a pressure differential in excess of a threshold.

20. The device of claim 11, further comprising a fluid flow path in fluid communication with said plurality of chambers, and wherein said fluid flow path is configured to provide reagents to said plurality of chambers.

21. The device of claim 1, wherein said chamber has a depth of less than or equal to about 500 micrometers.

22. The device of claim 11, wherein said chamber has a depth of less than or equal to about 500 micrometers.

23. The device of claim 1, further comprising a pressure unit configured to supply a pressure drop across said at least one gas permeable film or membrane, which pressure drop is sufficient to induce said gas flow from said chamber to said location external to said chamber.

24. The device of claim 11, further comprising a pressure unit configured to supply a pressure drop across said barrier, which pressure drop is sufficient to induce said gas flow from said chamber to said location external to said chamber.

25. The device of claim 6, wherein said polymer is an inelastic material.

26. The device of claim 6, wherein said polymer is a thermoplastic.

27. The device of claim 1, wherein said at least one gas permeable film or membrane is at least one gas permeable film.

28. The device of claim 1, wherein said at least one gas permeable film or membrane is at least one gas permeable membrane.

29. The device of claim 17, wherein said polymer is an inelastic material.

30. The device of claim 17, wherein said polymer is a thermoplastic.

* * * * *